United States Patent
Banba et al.

(10) Patent No.: US 12,104,124 B2
(45) Date of Patent: *Oct. 1, 2024

(54) APPARATUS AND METHOD FOR PRODUCING HYDROCARBONS

(71) Applicant: FURUKAWA ELECTRIC CO., LTD., Tokyo (JP)

(72) Inventors: Yuichiro Banba, Tokyo (JP); Kaori Sekine, Tokyo (JP); Yukako Nakai, Tokyo (JP); Mai Nishii, Tokyo (JP); Masayuki Fukushima, Tokyo (JP); Sadahiro Kato, Tokyo (JP); Takao Masuda, Sapporo (JP); Yuta Nakasaka, Sapporo (JP); Takuya Yoshikawa, Sapporo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 612 days.

This patent is subject to a terminal disclaimer.

(21) Appl. No.: 17/299,670

(22) PCT Filed: Dec. 3, 2019

(86) PCT No.: PCT/JP2019/047299
§ 371 (c)(1),
(2) Date: Jun. 3, 2021

(87) PCT Pub. No.: WO2020/116476
PCT Pub. Date: Jun. 11, 2020

(65) Prior Publication Data
US 2022/0033712 A1 Feb. 3, 2022

(30) Foreign Application Priority Data
Dec. 3, 2018 (JP) .................. 2018-226930

(51) Int. Cl.
*C10G 2/00* (2006.01)
*B01J 21/04* (2006.01)
(Continued)

(52) U.S. Cl.
CPC ................ *C10G 2/34* (2013.01); *B01J 21/04* (2013.01); *B01J 29/46* (2013.01); *B01J 35/19* (2024.01);
(Continued)

(58) Field of Classification Search
CPC ........ B01J 29/20; B01J 29/42; B01J 29/7215; B01J 29/7269; B01J 23/755; B01J 29/072;
(Continued)

(56) References Cited

U.S. PATENT DOCUMENTS

| 4,499,209 A | 2/1985 | Hoek et al. |
| 4,552,855 A | 11/1985 | Ozin et al. |

(Continued)

FOREIGN PATENT DOCUMENTS

| CA | 1 205 444 A | 6/1986 |
| CN | 108136379 A | 6/2018 |

(Continued)

OTHER PUBLICATIONS

Extended European Search Report issued Jul. 28, 2022 in European Patent Application No. 19891911.0, 9 pages.
(Continued)

*Primary Examiner* — Jafar F Parsa
(74) *Attorney, Agent, or Firm* — Oblon, McClelland, Maier & Neustadt, L.L.P.

(57) ABSTRACT

An apparatus and method for producing hydrocarbons including aromatic hydrocarbons and lower olefins including propylene from $CH_4$ and $CO_2$ through CO and $H_2$ with high activity and high selectivity. The apparatus is provided (Continued)

with: a synthetic gas production unit to which a gas containing $CH_4$ and $CO_2$ is supplied from a first supply unit, and which generates a synthetic gas containing CO and $H_2$ while heating a first catalyst structure; a production unit to which the synthetic gas is supplied and which generates hydrocarbons including aromatic hydrocarbons having 6-10 carbon atoms and lower olefins including propylene while heating a second catalyst structure; and a detection unit which detects propylene and the aromatic hydrocarbons discharged from the production unit, in which the first catalyst structure includes first supports having a porous structure and a first metal fine particle in the first supports, the first supports have a first channels, the first metal fine particle is present in the first channels, the second catalyst structure includes second supports having a porous structure and a second metal fine particle in the second supports, the second supports have a second channels, and a portion of the second channels have an average inner diameter of 0.95 nm or less.

20 Claims, 3 Drawing Sheets

(51) Int. Cl.
| | | |
|---|---|---|
| | *B01J 29/46* | (2006.01) |
| | *B01J 35/00* | (2024.01) |
| | *B01J 35/56* | (2024.01) |
| | *B01J 35/64* | (2024.01) |
| | *C01B 3/40* | (2006.01) |

(52) U.S. Cl.
CPC .............. *B01J 35/56* (2024.01); *B01J 35/643* (2024.01); *C01B 3/40* (2013.01); *C10G 2/334* (2013.01); *C01B 2203/0238* (2013.01); *C01B 2203/062* (2013.01); *C01B 2203/1005* (2013.01); *C01B 2203/1052* (2013.01); *C01B 2203/1082* (2013.01); *C10G 2300/4006* (2013.01); *C10G 2300/4025* (2013.01); *C10G 2300/70* (2013.01); *C10G 2400/20* (2013.01); *C10G 2400/30* (2013.01)

(58) Field of Classification Search
CPC .............. B01J 35/1057; B01J 2219/18; C10G 2300/4006; C10G 2300/4025; C10G 2300/70; C10G 2400/30; C10G 2400/20; C10G 2/334; C07C 2529/072; C07C 1/0435
See application file for complete search history.

(56) References Cited

U.S. PATENT DOCUMENTS

| | | |
|---|---|---|
| 2014/0303266 A1 | 10/2014 | Hyman |
| 2016/0296913 A1 | 10/2016 | Takahama et al. |
| 2018/0029024 A1 | 2/2018 | White et al. |
| 2018/0311651 A1 | 11/2018 | Ravon et al. |
| 2019/0039056 A1 | 2/2019 | Kato et al. |

FOREIGN PATENT DOCUMENTS

| | | | |
|---|---|---|---|
| EP | 0 455 307 | A1 | 11/1991 |
| EP | 3 632 544 | A1 | 4/2020 |
| EP | 3 632 546 | A1 | 4/2020 |
| JP | 59-102440 | A | 6/1984 |
| JP | 59-132940 | A | 7/1984 |
| JP | 4-227847 | A | 8/1992 |
| JP | 2005-15423 | A | 1/2005 |
| JP | 2013-255911 | A | 12/2013 |
| JP | 2014-534902 | A | 12/2014 |
| JP | 2016-2527 | A | 1/2016 |
| WO | WO 2009/051353 | A2 | 4/2009 |
| WO | WO 2013/057319 | A2 | 4/2013 |
| WO | WO 2014/142282 | A1 | 9/2014 |
| WO | WO 2015/072573 | A1 | 5/2015 |
| WO | WO 2017/072698 | A1 | 5/2017 |
| WO | WO 2018/221697 | A1 | 12/2018 |
| WO | WO 2018/221700 | A1 | 12/2018 |
| WO | WO 2020/027321 | A1 | 2/2020 |

OTHER PUBLICATIONS

Combined Chinese Office Action and Search Report issued Apr. 22, 2023 in Patent Application No. 201980077944.X (with English machine translation), 23 pages.
U.S. Appl. No. 17/299,674 filed Jun. 3, 2021, US 2022/0032252 A1, Banba, et al.
International Search Report issued on Mar. 3, 2020 in PCT/JP2019/047299 filed on Dec. 3, 2019, 3 pages.
Carvalho et al., "Design of nanocomposites with cobalt encapsulated in the zeolite micropores for selective synthesis of isoparaffins in Fischer-Tropsch reaction", Catalysis Science & Technology, vol. 7, No. 21, (2017), pp. 5019-5027, 9 total pages.
Laprune et al., "Highly Dispersed Nickel Particles Encapsulated in Multi-hollow Silicalite-1 Single Crystal Nanoboxes: Effects of Siliceous Deposits and Phosphorous Species on the Catalytic Performances", Chemcatchem, vol. 9, (2017), pp. 2297-2307, 12 total pages.
Japanese Office Action issued Aug. 8, 2023 in Japanese Patent Application No. 2020-559943, (with unedited computer-generated English Translation), 6 pages.

APPARATUS AND METHOD FOR PRODUCING HYDROCARBONS

TECHNICAL FIELD

The present invention relates to an apparatus and method for producing hydrocarbons.

BACKGROUND ART

In recent years, dry reforming has attracted attention as a countermeasure against global warming. Dry reforming is a technology that includes bringing carbon dioxide ($CO_2$), a substance responsible for global warming, into contact with methane ($CH_4$) to convert the carbon dioxide into a synthesis gas including carbon monoxide and hydrogen.

For example, Patent Document 1 discloses a catalyst for use in the production of such a synthesis gas, which includes a support of an oxygen-deficient perovskite complex oxide containing Mn and a certain alkaline earth metal; and nickel as a supported metal.

The reaction for producing a synthesis gas including carbon monoxide and hydrogen through contact between carbon dioxide and methane needs to be carried out at a temperature as high as 800° C. or more. Unfortunately, the catalyst disclosed in Patent Document 1 is not considered to have sufficient catalytic activity because the metal catalyst particles held on the surface of the support can easily aggregate at high temperature so that the catalytic activity can easily decrease.

For example, Patent Document 2 discloses a method for preventing adhesion between catalyst particles and increasing the specific surface area of catalyst particles, which includes fixing catalyst particles on the surface of a base material and then performing oxidation and reduction treatment under specific conditions.

Unfortunately, the catalyst structure disclosed in Patent Document 2, having the catalyst particles fixed on the base material surface, will also decrease in catalytic activity when placed in a high-temperature reaction field. To recover its catalytic function, therefore, the oxidation and reduction treatment needs to be performed again, which requires a complicated operation.

A known method of producing hydrocarbon compounds for use as raw materials for liquid or solid fuel products, such as synthetic fuels and synthetic oils as alternative fuels to petroleum, includes the Fischer-Tropsch synthesis reaction (hereinafter, also referred to as "FT synthesis reaction") by which hydrocarbons, specifically, liquid or solid hydrocarbons are catalytically produced from a synthesis gas composed mainly of carbon monoxide (CO) gas and hydrogen ($H_2$) gas.

Examples of the catalyst for use in the FT synthesis reaction include a catalyst disclosed in Patent Document 3, which includes a support, such as silica or alumina, and an active metal, such as cobalt or iron, on the support; and a catalyst disclosed in Patent Document 4, which includes cobalt, zirconium, or titanium, and silica.

The catalyst for use in the FT synthesis reaction can be obtained in the form of a supported cobalt or ruthenium oxide (unreduced catalyst) by, for example, impregnating a support, such as silica or alumina, with a cobalt or ruthenium salt and then calcining the impregnated support. The catalyst obtained in such a way should be made sufficiently active for the FT synthesis reaction. As disclosed in Patent Document 5, therefore, the obtained catalyst should be reduced by being brought into contact with a reducing gas, such as a hydrogen gas, so that the oxide of cobalt and/or ruthenium is converted into an active metal form.

During the FT synthesis reaction performed in a reactor, heavy hydrocarbons having a relatively large number of carbon atoms are produced mainly as liquid components while light hydrocarbons having a relatively small number of carbon atoms are produced mainly as gaseous components. Unfortunately, since hydrocarbons with various numbers of carbon atoms are synthesized during the FT synthesis reaction, the synthesis process needs to be followed by extra processes for obtaining desired hydrocarbons, such as cracking and purification processes. During the FT synthesis reaction, therefore, it is desirable to control as much as possible the distribution of the number of carbon atoms in the products.

Patent Document 6 discloses a core-shell catalyst including a core for serving as an FT synthesis catalyst; and a shell for cracking hydrocarbons to light ones, and discloses a technology using such a catalyst to allow the FT synthesis catalyst at the core to produce hydrocarbons and to allow the catalyst at the shell to crack the hydrocarbons, produced by the FT synthesis reaction, into light hydrocarbons. Unfortunately, Patent Document 6 only discloses the distribution of the number of carbon atoms in hydrocarbons mainly having five or more carbon atoms.

According to Patent Document 6, the number of carbon atoms in hydrocarbons produced at the core including a cobalt catalyst is controlled by the reaction at the surface of zeolite in the shell. Thus, even after the cracking of the products is controlled at the shell, the products may react again with the core or another adjacent shells. This makes it difficult to control the selectivity for hydrocarbons with the number of carbon atoms in a specific range, and specifically makes it difficult to control the distribution of the number of carbon atoms when light hydrocarbons with a small number of carbon atoms are to be produced.

Various aromatic hydrocarbons and light hydrocarbons, such as propylene and butene, produced as gaseous components during the FT synthesis reaction are known as basic raw materials for use in production of various chemicals. Although such compounds can be produced during the FT synthesis reaction, the selectivity for the production of such compounds still remains low. In other words, no techniques have been established for increasing the selectivity for such compounds produced by the FT synthesis reaction. A need also exists to develop such techniques not only for improving the compound selectivity but also for improving the production efficiency by omitting extra processes, such as purification, necessary after the synthesis process in the conventional art.

Patent Document 1: Japanese Unexamined Patent Application, Publication No. 2013-255911
Patent Document 2: Japanese Unexamined Patent Application, Publication No. 2016-2527
Patent Document 3: Japanese Unexamined Patent Application, Publication No. H04-227847
Patent Document 4: Japanese Unexamined Patent Application, Publication No. 559-102440
Patent Document 5: PCT International Publication No. WO2015/072573
Patent Document 6: PCT International Publication No. WO2014/142282

DISCLOSURE OF THE INVENTION

Problems to be Solved by the Invention

It is an object of the present invention to provide an apparatus and method for producing hydrocarbons, which make it possible to efficiently and highly selectively produce hydrocarbons including aromatic hydrocarbons and lower olefins including propylene from methane and carbon dioxide through production of a synthesis gas including carbon monoxide and hydrogen with less decrease in catalytic activity.

Means for Solving the Problems

The present invention has the following principal configuration.

1. An apparatus for producing hydrocarbons including lower olefins including propylene and aromatic hydrocarbons having six or more and ten or less carbon atoms, the apparatus including: a first supply unit that supplies a raw material gas including methane and carbon dioxide; a synthesis gas production unit that includes a first catalyst structure, receives supply of the raw material gas from the first supply unit, and produces a synthesis gas including carbon monoxide and hydrogen from methane and carbon dioxide in the raw material gas while heating the first catalyst structure; a second supply unit that supplies the synthesis gas discharged from the synthesis gas production unit; a hydrocarbon production unit that includes a second catalyst structure, receives supply of the synthesis gas from the second supply unit, and produces, from carbon monoxide and hydrogen in the synthesis gas, hydrocarbons including lower olefins including propylene and aromatic hydrocarbons having six or more and ten or less carbon atoms while heating the second catalyst structure; and a first detection unit that detects propylene and the aromatic hydrocarbons in the hydrocarbons discharged from the hydrocarbon production unit, wherein the first catalyst structure includes first supports each having a porous structure and including a zeolite-type compound, and at least one first catalytic material present in the first supports, the first supports have first channels communicating with outside the first supports, the first catalytic material is in the form of first metal fine particle and is present at least in the first channels of the first supports, the second catalyst structure includes second supports each having a porous structure and including a zeolite-type compound, and at least one second metal fine particle present in the second supports, the second supports have second channels communicating with outside the second supports, and some of the second channels have an average inner diameter of 0.95 nm or less.

2. The apparatus for producing hydrocarbons according to aspect 1, wherein the aromatic hydrocarbons include at least one of a polycyclic aromatic hydrocarbon and a compound represented by formula (1):

[Chem. 1]

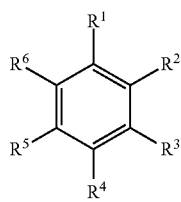

formula (1)

wherein $R^1$, $R^2$, $R^3$, $R^4$, $R^5$, and $R^6$ are each independently a hydrogen atom or an alkyl group having one or more and four or less carbon atoms.

3. The apparatus for producing hydrocarbons according to aspect 2, wherein the compound represented by formula (1) includes one or more compounds selected from the group consisting of benzene, toluene, and butylbenzene.

4. The apparatus for producing hydrocarbons according to aspect 2, wherein the polycyclic aromatic hydrocarbon includes at least one of azulene and naphthalene.

5. The apparatus for producing hydrocarbons according to any one of aspects 1 to 4, further including an oxygen supply unit that supplies oxygen to the synthesis gas production unit.

6. The apparatus for producing hydrocarbons according to aspect 5, wherein the oxygen supply unit supplies, to the synthesis gas production unit, oxygen at a concentration below an explosive limit.

7. The apparatus for producing hydrocarbons according to any one of aspects 1 to 6, wherein the synthesis gas production unit heats the first catalyst structure at 600° C. or more and 1000° C. or less.

8. The apparatus for producing hydrocarbons according to any one of aspects 1 to 7, wherein the first metal fine particle is a fine particle including at least one metal selected from the group consisting of rhodium (Rh), ruthenium (Ru), iridium (Ir), palladium (Pd), platinum (Pt), iron (Fe), cobalt (Co), and nickel (Ni).

9. The apparatus for producing hydrocarbons according to any one of aspects 1 to 8, wherein the first channels have any one of a one-dimensional pore, a two-dimensional pore, and a three-dimensional pore of a framework structure of the zeolite-type compound, and have a first enlarged pore portion different from the one-dimensional pore, the two-dimensional pore, and the three-dimensional pore, and the first catalytic material is present at least in the first enlarged pore portion.

10. The apparatus for producing hydrocarbons according to aspect 9, wherein the first enlarged pore portion connects a plurality of pores constituting any one of the one-dimensional pore, the two-dimensional pore, and the three-dimensional pore.

11. The apparatus for producing hydrocarbons according to aspect 9 or 10, wherein the first metal fine particle has an average particle size larger than an average inner diameter of the first channels and equal to or smaller than an inner diameter of the first enlarged pore portion.

12. The apparatus for producing hydrocarbons according to any one of aspects 1 to 11, further including a first separation unit that separates methane and carbon dioxide in the synthesis gas discharged from the synthesis gas production unit.

13. The apparatus for producing hydrocarbons according to aspect 12, further including a third supply unit that supplies, to the synthesis gas production unit, methane and carbon dioxide separated by the first separation unit.

14. The apparatus for producing hydrocarbons according to any one of aspects 1 to 13, further including a second detection unit that detects carbon monoxide and hydrogen in the synthesis gas discharged from the synthesis gas production unit.

15. The apparatus for producing hydrocarbons according to any one of aspects 1 to 14, wherein the hydrocarbon production unit heats the second catalyst structure at 350° C. or more and 550° C. or less.

16. The apparatus for producing hydrocarbons according to any one of aspects 1 to 15, wherein the second metal fine particle includes at least one first metal selected from the group consisting of ruthenium (Ru), nickel (Ni), iron (Fe), and cobalt (Co) or includes at least one first metal selected from the group consisting of ruthenium (Ru), nickel (Ni), iron (Fe), and cobalt (Co) and at least one second metal being different from the first metal and selected from the group consisting of platinum (Pt), palladium (Pd), gold (Au), silver (Ag), copper (Cu), ruthenium (Ru), iridium (Ir), rhodium (Rh), osmium (Os), zirconium (Zr), and manganese (Mn).

17. The apparatus for producing hydrocarbons according to any one of aspects 1 to 16, wherein some of the second channels have an average inner diameter of 0.39 nm or more and 0.75 nm or less.

18. The apparatus for producing hydrocarbons according to any one of aspects 1 to 17, wherein the second channels have any one of a one-dimensional pore, a two-dimensional pore, and a three-dimensional pore of a framework structure of the zeolite-type compound, and have a second enlarged pore portion different from the one-dimensional pore, the two-dimensional pore, and the three-dimensional pore, and the second metal fine particle is present at least in the second enlarged pore portion.

19. The apparatus for producing hydrocarbons according to aspects 1 to 18, further including a second separation unit that separates hydrogen, carbon monoxide, and the hydrocarbons discharged from the hydrocarbon production unit.

20. The apparatus for producing hydrocarbons according to aspect 19, further including a fourth supply unit that supplies, to the hydrocarbon production unit, carbon monoxide and hydrogen separated by the second separation unit.

21. The apparatus for producing hydrocarbons according to any one of aspects 1 to 20, further including a third separation unit that separates carbon dioxide, methane, and the hydrocarbons discharged from the hydrocarbon production unit.

22. The apparatus for producing hydrocarbons according to aspect 21, further including a fifth supply unit that supplies, to the synthesis gas production unit, methane and carbon dioxide separated by the third separation unit.

23. The apparatus for producing hydrocarbons according to any one of aspects 1 to 22, further including a fourth separation unit that cools the hydrocarbons discharged from the hydrocarbon production unit and separates the lower olefins and the aromatic hydrocarbons.

24. A method for producing hydrocarbons including lower olefins including propylene and aromatic hydrocarbons having six or more and ten or less carbon atoms, the method including: a step S1 that includes supplying, to a first catalyst structure, a raw material gas including methane and carbon dioxide; a step S2 that includes producing a synthesis gas including carbon monoxide and hydrogen from methane and carbon dioxide in the raw material gas while heating the first catalyst structure; a step S3 that includes supplying, to a second catalyst structure, the synthesis gas obtained in the step S2; a step S4 that includes producing, from carbon monoxide and hydrogen in the synthesis gas, hydrocarbons including lower olefins including propylene and aromatic hydrocarbons having six or more and ten or less carbon atoms while heating the second catalyst structure; and a step S5 that includes detecting propylene and the aromatic hydrocarbons in the hydrocarbons, wherein the first catalyst structure includes first supports each having a porous structure and including a zeolite-type compound, and at least one first catalytic material present in the first supports, the first supports have first channels communicating with outside the first supports, the first catalytic material is in the form of first metal fine particle and is present at least in the first channels of the first supports, the second catalyst structure includes second supports each having a porous structure and including a zeolite-type compound, and at least one second metal fine particles present in the second supports, the second supports have second channels communicating with outside the second supports, and some of the second channels have an average inner diameter of 0.95 nm or less.

Effects of the Invention

The present invention makes it possible to provide an apparatus and method for producing hydrocarbons, which make it possible to efficiently and highly selectively produce hydrocarbons including aromatic hydrocarbons and lower olefins including propylene from methane and carbon dioxide through production of a synthesis gas including carbon monoxide and hydrogen with less decrease in catalytic activity.

BRIEF DESCRIPTION OF THE DRAWINGS

FIGS. 2(a) and 2(b) are views schematically showing the inner structure of a first catalyst structure used in the apparatus for producing hydrocarbons, in which FIG. 2(a) is a perspective view (shown partially in transverse cross-sectional view), and FIG. 2(b) is a partially enlarged cross-sectional view.

PREFERRED MODE FOR CARRYING OUT THE INVENTION

Figure 1:
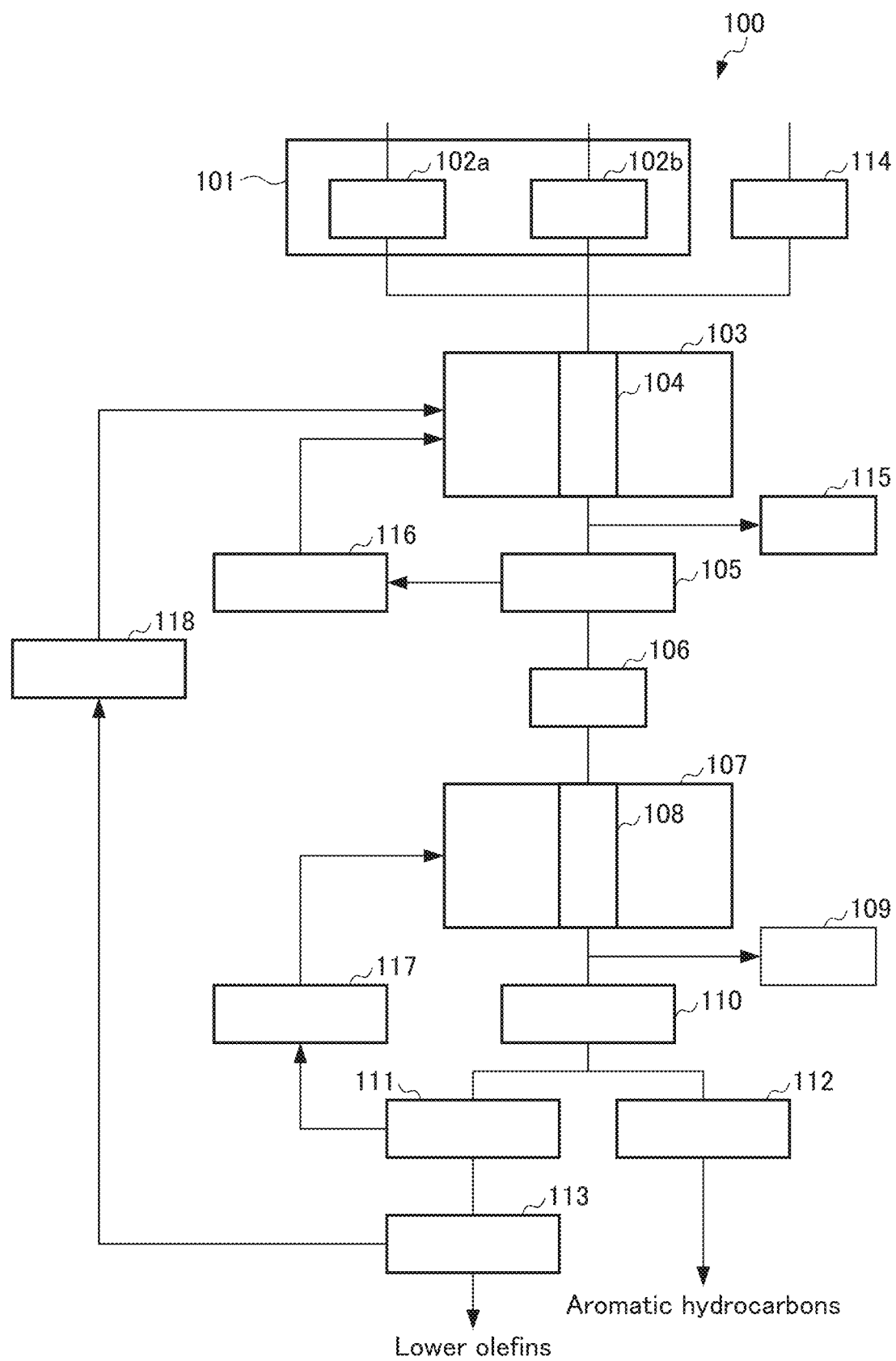
FIG. 1 is a block diagram showing, as blocks, principal components of an apparatus for producing hydrocarbons according to an embodiment.

Hereinafter, embodiments will be described with reference to the drawings.

As a result of intensive studies for achieving the object, the inventors have completed the present invention based on the findings that hydrocarbons including aromatic hydrocarbons and lower olefins including propylene can be efficiently produced with improved selectivity and less decrease in catalytic activity when the first and second catalyst structures are used.

The hydrocarbon production apparatus according to an embodiment is an apparatus for producing hydrocarbons including lower olefins including propylene and aromatic hydrocarbons having six or more and ten or less carbon atoms, the apparatus including: a first supply unit that supplies a raw material gas including methane and carbon dioxide; a synthesis gas production unit that includes a first catalyst structure, receives supply of the raw material gas from the first supply unit, and produces a synthesis gas including carbon monoxide and hydrogen from methane and carbon dioxide in the raw material gas while heating the first catalyst structure; a second supply unit that supplies the synthesis gas discharged from the synthesis gas production unit; a hydrocarbon production unit that includes a second catalyst structure, receives supply of the synthesis gas from the second supply unit, and produces, from carbon monoxide and hydrogen in the synthesis gas, hydrocarbons including lower olefins including propylene and aromatic hydrocarbons having six or more and ten or less carbon atoms while heating the second catalyst structure; and a first detection unit that detects propylene and the aromatic hydrocarbons in the hydrocarbons discharged from the hydrocarbon production unit, in which the first catalyst structure includes first supports each having a porous structure and including a zeolite-type compound, and at least one first catalytic material present in the first supports, the first supports have first channels communicating with outside the first supports, the first catalytic material is in the form of first metal fine particle and is present at least in the first channels of the first supports, the second catalyst structure includes second supports each having a porous structure and including a zeolite-type compound, and at least one second metal fine particle present in the second supports, the second supports have second channels communicating with outside the second supports, and some of the second channels have an average inner diameter of 0.95 nm or less.

The hydrocarbon production method according to another embodiment is a method for producing hydrocarbons including lower olefins including propylene and aromatic hydrocarbons having six or more and ten or less carbon atoms, the method including: a step S1 that includes supplying, to a first catalyst structure, a raw material gas including methane and carbon dioxide; a step S2 that includes producing a synthesis gas including carbon monoxide and hydrogen from methane and carbon dioxide in the raw material gas while heating the first catalyst structure; a step S3 that includes supplying, to a second catalyst structure, the synthesis gas obtained in the step S2; a step S4 that includes producing, from carbon monoxide and hydrogen in the synthesis gas, hydrocarbons including lower olefins including propylene and aromatic hydrocarbons having six or more and ten or less carbon atoms while heating the second catalyst structure; and a step S5 that includes detecting propylene and the aromatic hydrocarbons in the hydrocarbons, wherein the first catalyst structure includes first supports each having a porous structure and including a zeolite-type compound, and at least one first catalytic material present in the first supports, the first supports have first channels communicating with outside the first supports, the first catalytic material is in the form of first metal fine particle and is present at least in the first channels of the first supports, the second catalyst structure includes second supports each having a porous structure and including a zeolite-type compound, and at least one second metal fine particles present in the second supports, the second supports have second channels communicating with outside the second supports, and some of the second channels have an average inner diameter of 0.95 nm or less.

Configuration of Hydrocarbon Production Apparatus

FIG. 1 is a block diagram showing, as blocks, principal components of the hydrocarbon production apparatus according to an embodiment of the present invention.

As shown in FIG. 1, the hydrocarbon production apparatus 100 (hereinafter also simply referred to as "production apparatus") is an apparatus for producing hydrocarbons including lower olefins including propylene and aromatic hydrocarbons having six or more and ten or less carbon atoms and includes a first supply unit 101, a synthesis gas production unit 103, a second supply unit 106, a hydrocarbon production unit 107, and a first detection unit 109 as main components.

The first supply unit 101 includes a methane supply unit 102a and a carbon dioxide supply unit 102b and supplies, to the synthesis gas production unit 103, a raw material gas including methane and carbon dioxide. The methane supply unit 102a includes, for example, a methane gas cylinder or a methane gas generator and may be configured to control the supply of methane gas to the synthesis gas production unit 103. The carbon dioxide supply unit 102b includes, for example, a carbon dioxide gas cylinder or a carbon dioxide gas generator and may be configured to control the supply of carbon dioxide to the synthesis gas production unit 103.

The synthesis gas production unit 103 includes a first catalyst structure holder 104 that holds a first catalyst structure; and a heating unit (not shown), such as a heating furnace, and is configured to heat, at a predetermined temperature, the first catalyst structure in the first catalyst structure holder 104 by means of, for example, a heating furnace. The synthesis gas production unit 103 receives supply of the raw material gas including methane and carbon dioxide from the first supply unit 101, and produces a synthesis gas including carbon monoxide and hydrogen from methane and carbon dioxide in the raw material gas while heating the first catalyst structure in the first catalyst structure holder 104.

Specifically, while the raw material gas including methane and carbon dioxide is supplied from the first supply unit 101 to the synthesis gas production unit 103, the supplied methane and carbon dioxide are allowed to react with the first catalyst structure being heated in the synthesis gas production unit 103, so that a synthesis gas including carbon monoxide and hydrogen is produced. Hereinafter, the synthesis gas producing reaction occurring in the synthesis gas production unit 103 is also referred to as dry reforming reaction.

In the synthesis gas production unit 103, the first catalyst structure holder 104 may be installed in any manner that allows contact between the raw material gas and the first catalyst structure being heated in the first catalyst structure holder 104. As shown in FIG. 1, for example, the first catalyst structure holder 104 may be installed to connect the connecting portion between the piping for the raw material gas supply and the synthesis gas production unit 103 to the connecting portion between the synthesis gas production unit 103 and the synthesis gas discharge piping.

The second supply unit 106 supplies, to the hydrocarbon production unit 107, the synthesis gas including carbon monoxide and hydrogen, which is produced in and discharged from the synthesis gas production unit 103. The second supply unit 106 may be configured to control the supply of the synthesis gas to the hydrocarbon production unit 107.

The hydrocarbon production unit 107 includes a second catalyst structure holder 108 that holds a second catalyst structure; and a heating unit (not shown), such as a heating furnace, and is configured to heat, at a predetermined temperature, the second catalyst structure in the second catalyst structure holder 108 by means of, for example, a heating furnace. The hydrocarbon production unit 107 receives supply of the synthesis gas including carbon monoxide and hydrogen from the second supply unit 106, and produces hydrocarbons, from carbon monoxide and hydrogen in the synthesis gas, hydrocarbons including lower olefins including propylene and aromatic hydrocarbons having six or more and ten or less carbon atoms while heating the second catalyst structure in the second catalyst structure holder 108.

Specifically, while the synthesis gas including carbon monoxide and hydrogen is supplied from the second supply unit 106 to the hydrocarbon production unit 107, the supplied carbon monoxide and hydrogen are allowed to react with the second catalyst structure being heated in the hydrocarbon production unit 107, so that hydrocarbons including lower olefins including propylene and aromatic hydrocarbons having six or more and ten or less carbon atoms are produced. Hereinafter, the hydrocarbon producing reaction occurring in the hydrocarbon production unit 107 is also referred to as FT synthesis reaction.

In the hydrocarbon production unit 107, the second catalyst structure holder 108 may be installed in any manner that allows contact between the synthesis gas and the second catalyst structure being heated in the second catalyst structure holder 108. As shown in FIG. 1, for example, the second catalyst structure holder 108 may be installed to connect the connecting portion between the piping for the synthesis gas supply and the hydrocarbon production unit 107 to the connecting portion between the hydrocarbon production unit 107 and the hydrocarbon discharge piping.

The first detection unit 109 detects propylene and the aromatic hydrocarbons in the hydrocarbons produced in and discharged from the hydrocarbon production unit 107.

The hydrocarbons produced by the production apparatus 100 include propylene and the aromatic hydrocarbons. The concentrations of propylene and the aromatic hydrocarbons in the hydrocarbons may be at any levels and selected as appropriate by controlling the conditions for the dry reforming reaction and the FT synthesis reaction.

Besides propylene, the lower olefins in the hydrocarbons may include olefins having four or less carbon atoms, such as ethylene, propylene, and butene.

The aromatic hydrocarbons in the hydrocarbons may include at least one of a polycyclic aromatic hydrocarbon and a compound represented by formula (1):

[Chem. 2]

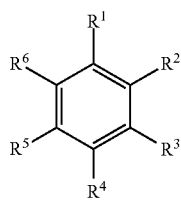

formula (1)

wherein $R^1$ to $R^6$ are each independently a hydrogen atom or an alkyl group having one or more and four or less carbon atoms.

The compound represented by formula (1) may include one or more selected from the group consisting of benzene, toluene, and butylbenzene. The polycyclic aromatic hydrocarbon may include at least one of azulene and naphthalene.

The hydrogen and carbon monoxide supplied to the second catalyst structure holder 108 preferably have a hydrogen/carbon monoxide molar ratio of 1.5 or more and 2.5 or less and more preferably 1.8 or more and 2.2 or less. The pressure (absolute pressure) in the second catalyst structure holder 108 is preferably 0.1 MPa or more and 3.0 MPa or less. Under such conditions, the FT synthesis reaction can efficiently proceed in the hydrocarbon production unit 107.

The production apparatus 100 uses the first and second catalyst structures to produce a synthesis gas including carbon monoxide and hydrogen from a raw material gas including methane and carbon dioxide and to produce, from the produced synthesis gas, hydrocarbons including lower olefins including propylene and aromatic hydrocarbons having six or more and ten or less carbon atoms. Thus, the production apparatus 100 allows direct use of the produced synthesis gas without any treatment of the synthesis gas produced from the raw material gas, such as addition or removal of materials and other composition modifications, which allows easy and convenient production of hydrocarbons.

The production apparatus 100 may further include a separate carbon monoxide supply unit (not shown) that supplies carbon monoxide to the hydrocarbon production unit 107; and a separate hydrogen supply unit (not shown) that supplies hydrogen to the hydrocarbon production unit 107 so that the synthesis gas produced from the raw material gas can be supplemented with carbon monoxide and hydrogen.

When the first detection unit 109 successfully detects propylene and the aromatic hydrocarbons in the hydrocarbons, the production apparatus 100 may be determined to be operating normally. When the first detection unit 109 fails to detect propylene and aromatic hydrocarbons in the hydrocarbons, the production apparatus 100 may be determined to be out of order, and at least one of the part involved in the dry reforming reaction and the part involved in the FT synthesis reaction should be deactivated and inspected or repaired.

The production apparatus 100 may further include an oxygen supply unit 114 that supplies oxygen to the synthesis gas production unit 103. The oxygen supply unit 114 may include, for example, an oxygen gas cylinder or an oxygen gas generator and may be configured to control the supply of oxygen gas to the synthesis gas production unit 103. After being supplied from the oxygen supply unit 114 to the synthesis gas production unit 103, oxygen may also be supplied to the hydrocarbon production unit 107 through the synthesis gas production unit 103.

The supply of oxygen from the oxygen supply unit 114 to the first and second catalyst structures in the first and second catalyst structure holders 104 and 108 can prevent a decrease in the catalytic activity of the first catalyst structure, which would otherwise be caused by dry reforming reaction-induced coking of the first catalyst structure, and prevent a decrease in the catalytic activity of the second catalyst structure, which would otherwise be caused by FT synthesis reaction-induced coking of the second catalyst structure.

The oxygen supply unit 114 preferably supplies, to the synthesis gas production unit 103, oxygen at a concentration below the explosive limit. The supply of oxygen at such a concentration to the synthesis gas production unit 103 can efficiently prevent a decrease in the catalytic activity of the first and second catalyst structures, which would otherwise be caused by coking.

Specifically, a larger amount of oxygen supplied to the synthesis gas production unit 103 can more effectively prevent the coking-induced deactivation of the first and second catalyst structures, in which the amount of oxygen should have an upper limit that makes the oxygen concentration lower than the explosive limit. Oxygen supplied from the oxygen supply unit 114 may be mixed with inert gas, such as nitrogen or argon, so that the oxygen concentration is adjusted to a predetermined level.

The synthesis gas production unit 103 preferably heats the first catalyst structure at 600° C. or more and 1000° C. or less. The heating of the first catalyst structure in the above temperature range allows the dry reforming reaction to proceed efficiently, which increases the production of carbon monoxide and hydrogen.

The production apparatus 100 may further include a first separation unit 105 that separates and collects the synthesis gas including carbon monoxide and hydrogen from the gas discharged from the synthesis gas production unit 103. The first separation unit 105 is preferably, for example, a cryogenic separation unit that separates the discharged gas into: a raw material gas fraction including methane and carbon dioxide remaining unreacted during the dry reforming reaction in the synthesis gas production unit 103; and a synthesis gas fraction including carbon monoxide and hydrogen. The separation of the raw material gas remaining unreacted in the discharged gas allows production of carbon monoxide and hydrogen at high volume contents, which increases the efficiency of the FT synthesis reaction.

The production apparatus 100 may further include a third supply unit 116 that supplies, to the synthesis gas production unit 103, the unreacted raw material gas separated by the first separation unit 105. The third supply unit 116 may be configured to control the supply of the raw material gas including methane and carbon dioxide to the synthesis gas production unit 103. The raw material gas supplied from the third supply unit 116 to the synthesis gas production unit 103 can be reused for the dry reforming reaction, which reduces the amount of the raw material gas used.

The production apparatus 100 may further include a second detection unit 115 that detects a synthesis gas (e.g., carbon monoxide and hydrogen) in the gas discharged from the synthesis gas production unit 103. When the second detection unit 115 successfully detects carbon monoxide and hydrogen in the synthesis gas, the dry reforming reaction may be determined to be proceeding normally. On the other hand, when the second detection unit 115 fails to detect carbon monoxide or hydrogen as a result of componential analysis of the discharged gas, the dry reforming reaction may be determined to be not proceeding, and the part involved in the dry reforming reaction should be deactivated and inspected or repaired.

The hydrocarbon production unit 107 heats the second catalyst structure preferably at 350° C. or more and 550° C. or less and more preferably at 450° C. or more and less than 550° C. The heating of the second catalyst structure in the above temperature range allows the FT synthesis reaction to selectively produce lower olefins, such as propylene, and the aromatic hydrocarbons, which increases the production of desired hydrocarbons.

The production apparatus 100 may further include a second separation unit 111 that separates and collects the hydrocarbons from the gas discharged from the hydrocarbon production unit 107. The second separation unit 111 is preferably, for example, a cryogenic separation unit that separates the discharged gas into: a synthesis gas fraction including carbon monoxide and hydrogen remaining unreacted during the FT synthesis reaction in the hydrocarbon production unit 107; and the hydrocarbons. The separation of the synthesis gas remaining unreacted in the discharged gas allows production of the hydrocarbons at a high-volume content.

The production apparatus 100 may further include a fourth supply unit 117 that supplies, to the hydrocarbon production unit 107, the unreacted synthesis gas separated by the second separation unit 111. The fourth supply unit 117 may be configured to control the supply of the synthesis gas (e.g., carbon monoxide and hydrogen) to the hydrocarbon production unit 107. Carbon monoxide and hydrogen supplied from the fourth supply unit 117 to the hydrocarbon production unit 107 can be reused for the FT synthesis reaction, which leads to a reduction in the amount of the raw material gas used.

The production apparatus 100 may further include a third separation unit 113 that separates the hydrocarbons and the unreacted raw material gas (e.g., methane and carbon dioxide) from the gas discharged from the hydrocarbon production unit 107. The third separation unit 113 may be, for example, a cryogenic separation unit that separates the discharged gas into: a raw material gas fraction remaining unreacted during the dry reforming reaction in the synthesis gas production unit 103; and the hydrocarbons. The separation of the raw material gas remaining unreacted in the discharged gas allows production of the hydrocarbons at a high volume content.

The production apparatus 100 may further include a fifth supply unit 118 that supplies, to the synthesis gas production unit 103, the unreacted raw material gas separated by the third separation unit 113. The fifth supply unit 118 may be configured to control the supply of the raw material gas (e.g., methane and carbon dioxide) to the synthesis gas production unit 103. Methane and carbon dioxide supplied from the fifth supply unit 118 to the synthesis gas production unit 103 can be reused for the dry reforming reaction, which reduces the amount of the raw material gas used.

The production apparatus 100 may further include a fourth separation unit 110 that cools the gas discharged from the hydrocarbon production unit 107 and separates the gas into: a gas fraction including lower olefins; and the aromatic hydrocarbons. The fourth separation unit 110 is, for example, a gas-liquid separator capable of cooling to room temperature. The gas fraction including lower olefins may include lower olefins, methane, carbon dioxide, carbon monoxide, and hydrogen.

The production apparatus 100 may further include a fifth separation unit 112 that separates water in the aromatic hydrocarbon fraction discharged from the fourth separation unit 110. The fifth separation unit 112 is, for example, a separator that performs fractional distillation according to boiling points. The water separated by the fifth separation unit 112 may be handled as industrial wastewater.

FIG. 1 shows an example in which methane and carbon dioxide are supplied respectively by the methane supply unit 102a and the carbon dioxide supply unit 102b. Alternatively, a gas of a mixture of methane and carbon dioxide may be supplied to the synthesis gas production unit 103. FIG. 1 also shows an example in which the raw material gas and oxygen are supplied respectively by the first supply unit 101 and the oxygen supply unit 114. Alternatively, a gas of a mixture of the raw material gas and oxygen may be supplied to the synthesis gas production unit 103.

The methane supply unit 102a may supply methane at any concentration, and the carbon dioxide supply unit 102b may supply carbon dioxide at any concentration. For example, the concentrations of methane and carbon dioxide may be 100% or adjusted to specific values by the mixing with inert gas, such as nitrogen or argon. When inert gas is used, an inert gas supply unit (not shown) may be provided to supply inert gas to the production apparatus 100.

FIG. 1 shows an example in which the first catalyst structure is installed in the first catalyst structure holder 104. The first catalyst structure may be installed in any manner that allows contact between the raw material gas and the first catalyst structure being heated. For example, the first catalyst structure may be held at part or across the whole of the synthesis gas production unit 103. Basically, similar to the first catalyst structure, the second catalyst structure may be installed in any manner that allows contact between the synthesis gas and the second catalyst structure being heated. For example, the second catalyst structure may be held at part or across the whole of the hydrocarbon production unit 107. The dry reforming reaction with the first catalyst structure and the FT synthesis reaction with the second catalyst structure may be carried out using, for example, a fixed bed, a supercritical fixed bed, a slurry bed, or a fluidized bed. In particular, a fixed bed, a supercritical fixed bed, or a slurry bed is preferred.

Regarding the arrangement of the second and third separation units 111 and 113, FIG. 1 shows an example in which the hydrocarbons are discharged from the second separation unit 111 and then supplied to the third separation unit 113. Alternatively, the positions of the second and third separation units 111 and 113 may be exchanged such that the hydrocarbons are discharged from the third separation unit 113 and then supplied to the second separation unit 111.

Regarding the location of the fourth separation unit 110, FIG. 1 shows an example in which the fourth separation unit 110 receives supply of the hydrocarbons discharged from the hydrocarbon production unit 107. Alternatively, the fourth separation unit 110 may be located to receive supply of the hydrocarbons discharged from the second separation unit 111 or the third separation unit 113. The production apparatus 100 may also include multiple sets of the fourth separation unit 110.

Method for Producing Hydrocarbons

The hydrocarbon production method according to an embodiment of the present invention is a method for producing hydrocarbons including lower olefins including propylene and aromatic hydrocarbons having six or more and ten or less carbon atoms, for example, which may be carried out using the production apparatus 100 shown in FIG. 1.

The hydrocarbon production method according to an embodiment of the present invention includes, as main steps, a first supply step S1, a first production step S2, a second supply step S3, a second production step S4, and a first detection step S5.

The first supply step S1 includes supplying, to a first catalyst structure, a raw material gas including methane and carbon dioxide. In the production apparatus 100 shown in FIG. 1, the raw material gas is supplied from the first supply unit 101 to the first catalyst structure in the first catalyst structure holder 104 provided inside the synthesis gas production unit 103.

The first production step S2 includes producing a synthesis gas including carbon monoxide and hydrogen from methane and carbon dioxide in the raw material gas supplied in the first supply step S1 while heating the first catalyst structure. In the production apparatus 100, a synthesis gas including carbon monoxide and hydrogen is produced from methane and carbon dioxide in the raw material gas using the first catalyst structure being heated at a predetermined temperature in the synthesis gas production unit 103.

The second supply step S3 includes supplying, to a second catalyst structure, the synthesis gas obtained in the first production step S2. In the production apparatus 100, the synthesis gas, which is produced in and discharged from the synthesis gas production unit 103, is supplied to the second catalyst structure in the second catalyst structure holder 108 provided inside the hydrocarbon production unit 107.

The second production step S4 includes producing hydrocarbons including lower olefins including propylene and aromatic hydrocarbons having six or more and ten or less carbon atoms from carbon monoxide and hydrogen in the synthesis gas supplied in the second supply step S3 while heating the second catalyst structure. In the production apparatus 100, the hydrocarbons are produced from carbon monoxide and hydrogen in the synthesis gas using the second catalyst structure being heated at a predetermined temperature in the hydrocarbon production unit 107.

The first detection step S5 includes detecting propylene and the aromatic hydrocarbons in the hydrocarbons produced in the second production step S4. In the production apparatus 100, the first detection unit 109 detects propylene and the aromatic hydrocarbons in the hydrocarbons, which are produced in and discharged from the hydrocarbon production unit 107.

The hydrocarbon production method according to an embodiment may further include an oxygen supply step S11 that includes supplying oxygen to the first and second catalyst structures. Oxygen is supplied from the oxygen supply unit 114 to the first and second catalyst structures respectively in the first and second catalyst structure holders 104 and 108. This can prevent a decrease in catalytic activity, which would otherwise be caused by coking of the first and second catalyst structures, in the first and second production steps S2 and S4.

The hydrocarbon production method according to an embodiment may further include a first separation step S12 that includes separating methane and carbon dioxide from the synthesis gas produced in the first production step S2. The first separation unit 105 can separate methane and carbon dioxide from the synthesis gas produced in the first production step S2, so that the FT synthesis reaction can be carried out with higher efficiency in the second production step S4.

The hydrocarbon production method according to an embodiment may further include a third supply step S13 that includes feeding, to the first production step S2, methane and carbon dioxide separated in the first separation step S12. The third supply unit 116 can feed methane and carbon dioxide to the first production step S2 so that the raw material gas including methane and carbon dioxide can be reused for the dry reforming reaction in the first production step S2.

The hydrocarbon production method according to an embodiment may further include a second detection step S14 that includes detecting carbon monoxide and hydrogen in the synthesis gas produced in the first production step S2. The second detection unit 115 can detect carbon monoxide and hydrogen in the synthesis gas produced in the first production step S2.

The hydrocarbon production method according to an embodiment may further include a second separation step S15 that includes separating carbon monoxide and hydrogen from the hydrocarbons produced in the second production step S4. The second separation unit 111 can separate carbon monoxide and hydrogen from the hydrocarbons produced in the second production step S4, so that the hydrocarbons can be produced at a higher volume content.

The hydrocarbon production method according to an embodiment may further include a fourth supply step S16 that includes feeding, to the second production step S4, carbon monoxide and hydrogen separated in the second separation step S15. The fourth supply unit 117 can feed, to the second production step S4, the unreacted synthesis gas including carbon monoxide and hydrogen, which can be reused for the FT synthesis reaction in the second production step S4.

The hydrocarbon production method according to an embodiment may further include a third separation step S17 that includes separating methane and carbon dioxide from the hydrocarbons discharged during the second production step S4. The third separation unit 113 can separate methane and carbon dioxide from the hydrocarbons so that the hydrocarbons can be produced at a higher volume content.

The hydrocarbon production method according to an embodiment may further include a fifth supply step S18 that includes feeding, to the first production step S2, methane and carbon dioxide separated in the third separation step S17. The fifth supply unit 118 can feed, to the first production step S2, the unreacted raw material gas including methane and carbon dioxide, which can be reused for the dry reforming reaction in the first production step S2.

The hydrocarbon production method according to an embodiment may further include a fourth separation step S19 that includes cooling the hydrocarbons produced in the second production step S4 and separates the hydrocarbons into a gas fraction including the lower olefins; and the aromatic hydrocarbons. The fourth separation unit 110 can cool the hydrocarbons and thus separate the lower olefins and the aromatic hydrocarbons.

The hydrocarbon production method according to an embodiment may further include a fifth separation step S20 that includes separating water in the aromatic hydrocarbon fraction obtained during the fourth separation step S19. The fifth separation unit 112 can separate water in the aromatic hydrocarbon fraction obtained during the fourth separation step S19.

Figure 2A:
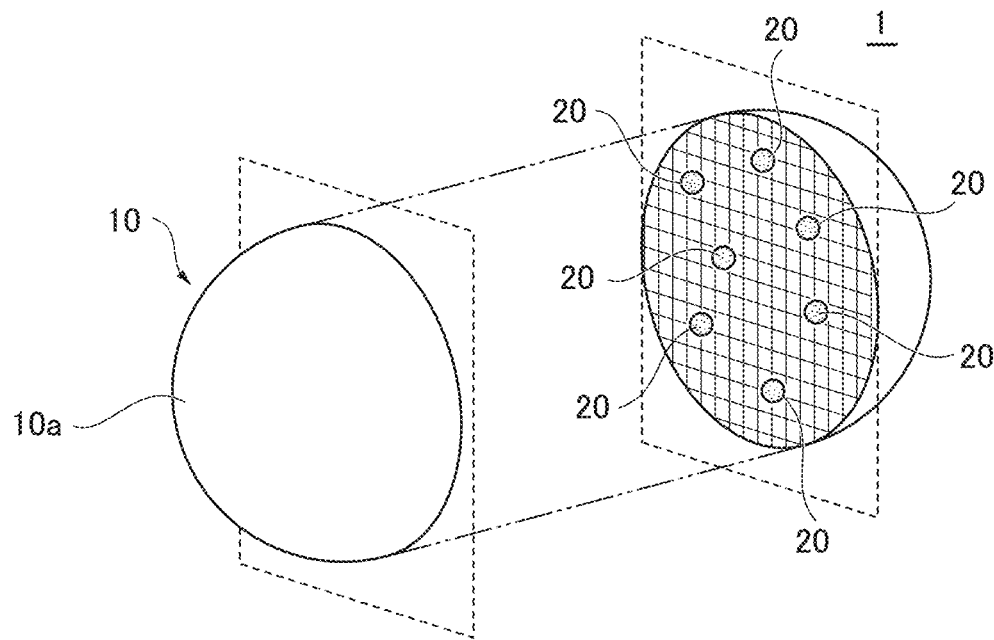
Figure 2B:
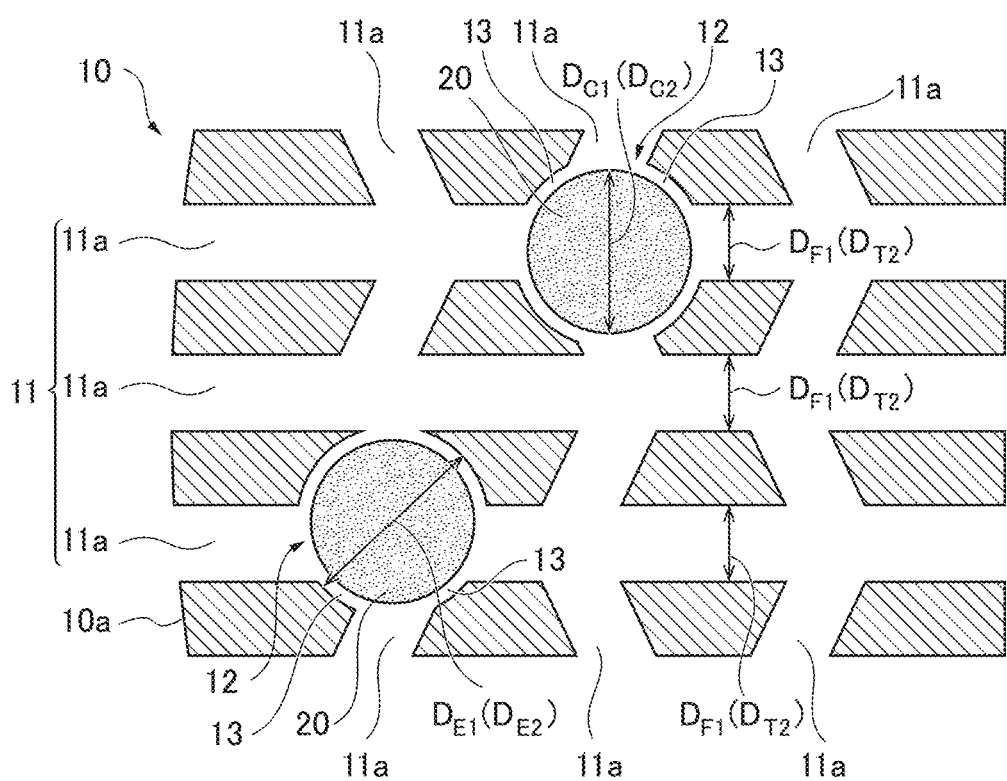

Configuration of First Catalyst structure FIGS. 2(a) and 2(b) are views schematically showing the configuration of the first catalyst structure 1 held in the first catalyst structure holder 104 of the hydrocarbon production apparatus 100 described above, in which FIG. 2(a) is a perspective view (shown partially in transverse cross-sectional view), and FIG. 2(b) is a partially enlarged cross-sectional view. It should be noted that FIGS. 2(a) and 2(b) show only an example of the first catalyst structure and the configuration shown in FIGS. 2(a) and 2(b), such as shapes and dimensions, are not intended to limit those of the present invention. The first catalyst structure 1 is suitable for use in dry reforming reaction.

As shown in FIG. 2 (a), the first catalyst structure 1 includes a first support 10 having a porous structure and including a zeolite-type compound; and at least one first catalytic material 20 present in the first support 10.

In the first catalyst structure 1, the multiple first catalytic material 20 are included in the porous structure of the first support 10. The first catalytic material 20 may be any material having a catalytic ability (catalytic activity) and may be specifically in the form of first metal fine particles. The first metal fine particles will be described in detail later.

As shown in FIG. 2(b), the first support 10 has a porous structure and has first channels 11 communicating with one another and communicating with outside the first support 10. The first support 10 preferably has multiple first pores 11a, which form the first channels 11. The first catalytic material 20 is present at least in first channels 11 of the first support 10 and is preferably held at least in first channels 11 of the first support 10.

Such a configuration restricts the movement of the first catalytic material 20 in the first support 10 and effectively prevents aggregation of the first catalytic material 20. This results in effective prevention of a decrease in the effective surface area of the first catalytic material 20 and results in long-term retention of the catalytic activity of the first catalytic material 20. In other words, the configuration of the first catalyst structure 1 make it possible to prevent a decrease in catalytic activity, which would otherwise be caused by aggregation of the first catalytic material 20, and to prolong the life of the first catalyst structure 1. Moreover, thanks to the prolonged life of the first catalyst structure 1, the frequency of replacement of the first catalyst structure 1 can be reduced, and the amount of discarding of the used first catalyst structure 1 can be greatly reduced, which leads to resource saving.

In general, when used in a fluid, the first catalyst structure may receive an external force from the fluid. In such a case, if a first catalytic material is only deposited on the outer surface of the first support 10, there will be a problem in that, due to the influence of the external force from the fluid, the first catalytic material can easily separate from the outer surface of the first support 10. On the other hand, in the first catalyst structure 1, the first catalytic material 20 is present at least in first channels 11 of the first support 10 and thus less likely to separate from the first support 10 even when receiving an external force from a fluid.

Specifically, when the first catalyst structure 1 is placed in a fluid, the fluid flowing into the first channels 11 through the first pores 11a of the first support 10 encounters flow channel resistance (frictional force), so that the velocity of the fluid flowing in the first channels 11 would be lower than that of the fluid flowing on the outer surface of the first support 10. Due to the influence of such flow channel resistance, the pressure applied from the fluid onto the first catalytic material 20 present in the first channels 11 becomes lower than that applied outside the first support 10.

Therefore, the first catalytic material 20 is effectively prevented from separating from the first support 11, and the catalytic activity of the first catalytic material 20 can be stably maintained for a long period of time. The flow channel resistance would be higher when the channel 11 of the first support 10 has multiple curves or branches and the interior of the first support 10 has a more complicated three-dimensional structure.

The first channels 11 preferably have any one of a one-dimensional pore, a two-dimensional pore, and a three-dimensional pore, which are defined by the framework structure of the zeolite-type compound, and preferably have a first enlarged pore portion 12 different from the one-dimensional pore, the two-dimensional pore, and the three-dimensional pore. In this case, the first catalytic material 20 is preferably present at least in the first enlarged pore portion 12 and more preferably included at least in the first enlarged pore portion 12.

According to this configuration, the movement of the first catalytic material 20 is further restricted in the first support 10, and separation of the first catalytic material 20 and aggregation of the first catalytic material 20 are more effectively prevented. The state in which the catalytic material 20 is included in the porous structure of the support 10 indicates that the catalytic material 20 is enclosed within the support 10. In this regard, the first catalytic material 20 and the first support 10 do not always have to be in direct contact with each other, and the first catalytic material 20 may be indirectly held by the first support 10 with an additional material (e.g., a surfactant) provided between the first catalytic material 20 and the first support 10.

As used herein, the term "one-dimensional pore" or "one-dimensional pores" refers to a tunnel- or cage-shaped pore that forms a one-dimensional channel or refers to multiple tunnel- or cage-shaped pores that form multiple one-dimensional channels. The term "two-dimensional pore" refers to a channel having multiple one-dimensional channels connected two-dimensionally. The term "three-dimensional pore" refers to a channel having multiple one-dimensional channels connected three-dimensionally.

FIG. 2(b) shows a case in which the first catalytic material 20 is included in the first enlarged pore portion 12. Such a configuration is non-limiting, and alternatively, the first catalytic material 20 may be held in the first channel 11 while partially protruding out of the first enlarged pore portion 12. Alternatively, the first catalytic material 20 may be partially embedded in a portion of the first channel 11 other than the first enlarged pore portion 12 (e.g., an inner wall portion of the first channel 11) or may be held by fixation or the like.

The first enlarged pore portion 12 also preferably connects multiple first pores 11a to one another when the first pores 11a form any of the one-dimensional pore, the two-dimensional pore, and the three-dimensional pore. According to this configuration, another channel different from the one-dimensional pore, the two-dimensional pore, or the three-dimensional pore is provided in the first support 10 to exert the function of the first catalytic material 20 more effectively.

The first channel 11 preferably has a three-dimensional structure including a branching or junction portion inside the first support 10, and the first enlarged pore portion 12 is preferably provided at the branching or junction portion of the first channel 11.

The average inner diameter $D_{F1}$ of the first channels 11 provided in the first support 10 may be calculated from the average of the short and long diameters of the first pores 11a, which form any of the one-dimensional pore, the two-dimensional pore, and the three-dimensional pore. The average inner diameter $D_{F1}$ of the first channels 11 is typically 0.1 nm or more and 1.5 nm or less and preferably 0.5 nm or more and 0.8 nm or less. The inner diameter $D_{E1}$ of the first enlarged pore portion 12 is typically 0.5 nm or more and 50 nm or less, preferably 1.1 nm or more and 40 nm or less, and more preferably 1.1 nm or more and 3.3 nm or less. The inner diameter $D_{E1}$ of the first enlarged pore portion 12 depends, for example, on the pore size of the first precursor material (A1) described later and the average particle size $D_{C1}$ of the first catalytic material 20 to be included. The inner diameter $D_{F1}$ of the first enlarged pore portion 12 is such that it is possible to include the first catalytic material 20.

The first support 10 includes a zeolite-type compound. Examples of the zeolite-type compound include silicate compounds, such as zeolite (aluminosilicate), cation-exchanged zeolite, and silicalite; zeolite analogue compounds, such as aluminoborates, aluminoarsenates, and germanates; and phosphate-based zeolite analogue materials, such as molybdenum phosphate. Among them, the zeolite-type compound is preferably a silicate compound.

The framework structure of the zeolite-type compound may be selected from FAU type (Y or X type), MTW type, MFI type (ZSM-5), FER type (ferrierite), LTA type (A type), MWW type (MCM-22), MOR type (mordenite), LTL type (L type), BEA type (beta type), and so on, and is preferably MFI type and more preferably ZSM-5. The zeolite-type compound has multiple pores with a diameter depending on its framework structure. For example, an MFI-type zeolite compound has a maximum pore size of 0.636 nm (6.36 Å) and an average pore size of 0.560 nm (5.60 Å).

Hereinafter, the first catalytic material 20 will be described in detail. The first catalytic material 20 is in the form of first metal fine particles. The first metal fine particles may be held in the form of primary particles in the first channels 11 or may be held in the form of secondary particles, which result from aggregation of the primary particles, in the first channels 11. In both cases, the first metal fine particles preferably have an average particle size $D_{C1}$ larger than the average inner diameter $D_{F1}$ of the first channels 11 and equal to or smaller than the inner diameter $D_{E1}$ of the first enlarged pore portion 12 ($D_{F1} < D_{C1} < D_{F1}$). The first catalytic material 20 with such configuration is preferably included in the first enlarged pore portion 12 in the first channel 11, so that the movement of the first catalytic material 20 is restricted in the first support 10. Therefore, even when an external force is applied from a fluid to the first catalytic material 20, the movement of the first catalytic material 20 is suppressed in the first support 10, so that the first catalytic materials 20, 20 . . . dispersed in first channels 11 of the first support 10 and respectively included in the first enlarged pore portions 12, 12 . . . are effectively prevented from coming into contact with one another.

The average particle size $D_{C1}$ of the first metal fine particles is preferably 1 nm or more and 13.0 nm or less. The catalytic activity of the first metal fine particles with an average particle size $D_{C1}$ in the above range will sufficiently increase as the average particle size $D_{C1}$ decreases. In view of both high catalytic activity and anti-coking, the average particle size $D_{C1}$ of the first metal fine particles is preferably 9.0 nm or less and more preferably 4.5 nm or less. When the first metal fine particles are fine particles of at least one metal selected from the group consisting of iron (Fe), cobalt (Co), and nickel (Ni) as mentioned below, the first metal fine particles with an average particle size $D_{C1}$ in the above range can have a sufficiently high level of catalytic activity and anti-coking properties.

When the first catalytic material 20 is in the form of first metal fine particles, the content of a first metal element (M1) of the first metal fine particles is preferably 0.5 mass % or more and 7.6 mass % or less, more preferably 0.5 mass % or more and 6.9 mass % or less, even more preferably 0.5 mass % or more and 2.5 mass % or less, and most preferably 0.5 mass % or more and 1.5 mass % or less based on the mass of the first catalyst structure 1. For example, when the first metal element (M1) is Ni, the content (mass %) of the Ni element is expressed by {(the mass of Ni element)/(the mass of all elements in the first catalyst structure 1)}×100.

The first metal fine particles only have to include metal that is intact and not oxidized. For example, the first metal fine particles may include a single metal or a mixture of two or more metals. When used herein to indicate the component (material) of the first metal fine particles, the term "metal" is a generic term for a metallic material including one or more first metal elements, which is intended to include an elementary metal including a single first metal element (M1) and an alloy including two or more first metal elements (M1). In the environment where the catalyst structure is used, an oxide of the first metal element can be reduced to first metal fine particles. In such a case, the metal oxide may be deemed to be equivalent to first metal fine particles.

Examples of such metal include rhodium (Rh), ruthenium (Ru), iridium (Ir), palladium (Pd), platinum (Pt), molybdenum (Mo), tungsten (W), iron (Fe), cobalt (Co), chromium (Cr), cerium (Ce), copper (Cu), magnesium (Mg), aluminum (Al), and nickel (Ni). The first metal fine particles are preferably composed mainly of one or more of them. Particularly for catalytic activity, the first metal fine particles are preferably fine particles including at least one metal selected from the group consisting of rhodium (Rh), ruthenium (Ru), iridium (Ir), palladium (Pd), platinum (Pt), iron (Fe), cobalt (Co), and nickel (Ni), and more preferably including at least one metal selected from the group consisting of rhodium (Rh), ruthenium (Ru), iridium (Ir), and nickel (Ni). In particular, nickel (Ni) is preferred in terms of cost and performance.

The ratio (Si/M atomic ratio) of the number of silicon (Si) atoms in the first support 10 to the number of the first metal element (M1) in the first metal fine particles is preferably 10 or more and 1000 or less and more preferably 50 or more and 200 or less. If the ratio is higher than 1000, the first metal fine particles may have low catalytic activity or fail to act sufficiently as a catalytic material. If the ratio is lower than 10, the content of the first metal fine particles may be so high as to tend to reduce the strength of the first support 10. It should be noted that, in this context, the term "first metal fine particles 20" refers to fine particles provided or held inside the first support 10 and is not intended to include metal fine particles deposited on the outer surface of the first support 10.

Function of First Catalyst structure

As mentioned above, the first catalyst structure 1 includes a first support 10 of a porous structure and at least one first catalytic material 20 in the first support 10. When brought into contact with a fluid, the first catalyst structure 1 exerts the catalytic ability of the first catalytic material 20 in the first support 10. Specifically, when coming into contact with the first outer surface 10a of the first catalyst structure 1, the fluid is allowed to flow into the interior of the first support 10 through a first pore 11a at the first outer surface 10a, guided into the first channels 11, and allowed to pass through the first channels 11 and to flow out of the first catalyst structure 1 through another first pore 11a. The first catalytic material 20 in the first channel 11 causes a catalytic reaction when coming into contact with the fluid passing through the first channel 11. The first catalyst structure 1 also has a molecular sieving ability since the support has a porous structure.

First, the molecular sieving ability of the first catalyst structure 1 will be described with reference to an example in which the fluid includes a methane-containing gas and carbon dioxide. Herein, the term "methane-containing gas" refers to a mixed gas including methane and a non-methane gas. The first catalyst structure 1 may be brought into contact with the methane-containing gas and carbon dioxide sequentially or simultaneously.

Compound molecules (e.g., methane and carbon dioxide) having a size equal to or smaller than the diameter of the first pore 11a, in other words, equal to or smaller than the inner diameter of the first channel 11, can flow into the first support 10. On the other hand, gas component molecules having a size exceeding the diameter of the first pore 11a cannot flow into the first support 10. Accordingly, among multiple compounds in the fluid, some compounds not capable of flowing into the first support 10 are restricted from reacting, and some other compounds capable of flowing into the first support 10 are allowed to react. In this embodiment, the reaction proceeds between methane and carbon dioxide.

Among compounds produced by reactions in the first support 10, only compounds having a molecular size not exceeding the diameter of the first pore 11a can pass through the first pore 11a to outside the first support 10 to obtain a reaction product. On the other hand, some compounds are not capable of passing through the first pore 11a to outside the first support 10. If such compounds are converted into compounds having a molecular size that allows exit from the first support 10, the compounds can go outside the first support 10. As a result, the use of the first catalyst structure 1 makes it possible to selectively obtain a specific reaction product. In this embodiment, specifically, methane and carbon dioxide react to yield a synthesis gas as a reaction product, which includes carbon monoxide and hydrogen.

In the first catalyst structure 1, the first catalytic material 20 is included in the first enlarged pore portion 12 of the first channel 11. When the average particle size $D_{C1}$ of the first catalytic material 20 (metal fine particles) is larger than the average inner diameter $D_{F1}$ of the first channel 11 and smaller than the inner diameter $D_{E1}$ of the first enlarged pore portion 12 ($D_{F1} < D_{C1} < D_{E1}$), a small first channel 13 is provided between the first catalytic material 20 and the first enlarged pore portion 12. In this case, the fluid entering the first small channel 13 comes into contact with the first catalytic material 20. Each piece of the first catalytic material 20 included in the first enlarged pore portion 12 is restricted from moving in the first support 10. Thus, the first catalytic material 20 are prevented from aggregating in the first support 10. As a result, a large contact area can be stably maintained between the first catalytic material 20 and the fluid.

In an embodiment of the present invention using the first catalyst structure 1, a synthesis gas including carbon monoxide and hydrogen can be produced from a methane-containing gas and carbon dioxide as raw materials. The catalytic reaction, although carried out at a high temperature, preferably 600° C. or more and 1000° C. or less or 800° C. or more, is less affected by the heating, since the first catalytic material 20 is incorporated in the first support 10. As a result, a decrease in catalytic activity is prevented, which allows the first catalyst structure 1 to have a longer life.

Method of Producing First Catalyst structure

Hereinafter, an example of a method of producing the first catalyst structure 1 will be described with reference to an example in which the first catalytic material 20 in the first support is in the form of metal fine particles.

Step S1-1: Preparation Step

First, a first precursor material (A1) is prepared, which is for forming a first support having a porous structure and including a zeolite-type compound. The precursor material (A1) is preferably an ordered mesoporous material, and may be appropriately selected depending on the type (composition) of the zeolite-type compound for forming the first support of the first catalyst structure.

When a silicate compound is used as the zeolite-type compound for forming the first support of the first catalyst structure, the ordered mesoporous material is preferably a compound having an Si—O framework having pores with a diameter of 1 nm or more and 50 nm of less uniformly and regularly developed in a one-dimensional pattern, a two-dimensional pattern, or a three-dimensional pattern. A variety of synthetic products can be obtained as such ordered mesoporous materials depending on the synthesis conditions. Examples of such synthetic products include SBA-1, SBA-15, SBA-16, KIT-6, FSM-16, and MCM-41. In particular, MCM-41 is preferred. For reference, SBA-1 has a pore size of 10 nm or more and 30 nm or less, SBA-15 has a pore size of 6 nm or more and 10 nm or less, SBA-16 has a pore size of 6 nm, KIT-6 has a pore size of 9 nm, FSM-16 has a pore size of 3 nm or more and 5 nm or less, and MCM-41 has a pore size of 1 nm or more and 10 nm or less. Examples of such an ordered mesoporous material include mesoporous silica, mesoporous aluminosilicate, and mesoporous metallosilicate.

The first precursor material (A1) may be any of a commercially available product and a synthetic product. The precursor material (A1) may be synthesized using a known method for synthesizing an ordered mesoporous material. For example, a mixture solution is prepared, which contains a raw material containing elements for forming the first precursor material (A1) and a template agent for directing the structure of the first precursor material (A1). Optionally after being subjected to pH adjustment, the mixture solution is subjected to hydrothermal treatment (hydrothermal synthesis). Subsequently, the precipitate (product) resulting from the hydrothermal treatment is collected (e.g., filtered off), washed and dried if necessary, and then calcinated to obtain a first precursor material (A1) as a powdery ordered mesoporous material. In this process, the solvent for the mixture solution may be, for example, water, an organic solvent such as an alcohol, or a mixed solvent thereof. The raw material may be selected depending on the type of the first support. Examples of the raw material include silica agents, such as tetraethoxysilane (TEOS), fumed silica, and quartz sand. The template agent may be any of various surfactants and block copolymers. The template agent is preferably selected depending on the type of the ordered mesoporous material to be synthesized. For example, the template agent for use in forming MCM-41 is preferably a surfactant such as hexadecyltrimethylammonium bromide. The hydrothermal treatment may be performed, for example, in a closed vessel under conditions at 80° C. or more and 800° C. or less and 0 kPa or more and 2000 kPa or less for 5 hours or more and 240 hours or less. The calcining treatment may be performed, for example, in the air under conditions at 350° C. or more and 850° C. or less for 2 hour or more and 30 hours or less.

Step S1-2: Impregnation Step

Next, the prepared first precursor material (A1) is impregnated with a first metal-containing solution to form a first precursor material (B1).

The first metal-containing solution may be any solution containing a metal component (e.g., metal ions) corresponding to the first metal element (M1) for forming the first metal fine particles. For example, the first metal-containing solution may be prepared by dissolving, in a solvent, a metal salt containing the first metal element (M1). Examples of such a metal salt include chlorides, hydroxides, oxides, sulfates, and nitrates, among which nitrates are preferred. The solvent may be, for example, water, an organic solvent such as an alcohol, or a mixture solvent thereof.

Any method may be used to impregnate the first precursor material (A1) with the first metal-containing solution. For example, before the calcining step S1-3 described later, the impregnation is preferably performed by adding the first metal-containing solution little by little in multiple portions to the powdery first precursor material (A1) being stirred. In order to allow the first metal-containing solution to more easily enter the inner pores of the first precursor material (A1), a surfactant is preferably added as an additive to the first precursor material (A1) in advance before the addition of the first metal-containing solution. Such an additive can act to cover the outer surface of the first precursor material (A1) and thus to inhibit the deposition of the first metal-containing solution on the outer surface of the first precursor material (A1), so that the first metal-containing solution added subsequently could easily enter the pores of the first precursor material (A1).

Examples of such an additive include nonionic surfactants such as polyoxyethylene alkyl ethers, such as polyoxyethylene oleyl ether, and polyoxyethylene alkyl phenyl ether. These surfactants have a large molecular size and thus cannot enter the inner pores of the first precursor material (A1), which suggests that they will not adhere to the interior of the pores and will not hinder the entrance of the first metal-containing solution into the pores. A method of adding the nonionic surfactant preferably includes, for example, adding 50 mass % or more and 500 mass % or less of the nonionic surfactant to the first precursor material (A1) before the calcining step S1-3 described later. If the amount of the nonionic surfactant added to the first precursor material (A1) is less than 50 mass %, the inhibiting effect may be difficult to achieve, and if the amount of the nonionic surfactant is more than 500 mass % relative to the amount of the first precursor material (A1), the solution may have undesirably high viscosity. Therefore, the amount of the nonionic surfactant added to the first precursor material (A1) should be set to a value within the above range.

The amount of the first metal element (M1) in the first metal-containing solution, with which the first precursor material (A1) is to be impregnated (in other words, the amount of the first metal element (M1) to be incorporated into the first precursor material (B1)) is preferably taken into account when the amount of the first metal-containing solution added to the first precursor material (A1) is appropriately adjusted. For example, before the calcining step S1-3 described later, the amount of the first metal-containing solution added to the first precursor material (A1) is preferably adjusted such that the ratio ($Si/M_1$ atomic ratio) of the number of silicon (Si) atoms in the first precursor material (A1) to the number of the first metal element (M1) in the first metal-containing solution is set to 10 or more and 1000 or less and more preferably 50 or more and 200 or less. For example, when a surfactant is added as an additive to the first precursor material (A1) before the addition of the first metal-containing solution to the first precursor material (A1), the amount of the first metal-containing solution added to the first precursor material (A1) may be adjusted such that the calculated Si/M atomic ratio can be 50 or more and 200 or less. In such a case, the content of the first metal element (M1) of the first metal fine particles can be adjusted to 0.5 mass % or more and 7.6 mass % or less based on the mass of the first catalyst structure 1. In the first precursor material (B1), the content of the first metal element (M1) in the inner porous portion is approximately proportional to the amount of the first metal-containing solution added to the first precursor material (A1) as long as the metal concentration of the first metal-containing solution, the presence or absence of the additive, and other conditions such as temperature and pressure remain constant. The amount of the first metal element (M1) in the first precursor material (B1) is also proportional to the amount of the first metal element (M1) in the first metal fine particles in the first support of the first catalyst structure. Accordingly, when the amount of the first metal-containing solution added to the first precursor material (A1) is controlled within the above range, the inner pores of the first precursor material (A1) can be impregnated with a sufficient amount of the first metal-containing solution, which makes it possible to adjust the content of the first metal fine particles in the first support of the first catalyst structure.

After the first precursor material (A1) is impregnated with the first metal-containing solution, washing treatment may be performed if necessary. The washing liquid used may be water, an organic solvent such as an alcohol, or a mixed solution thereof. Drying treatment is also preferably performed after the impregnation of the first precursor material (A) with the first metal-containing solution and optionally after the washing treatment. The drying treatment may include natural drying overnight or so or drying at a high temperature of 150° C. or less. The drying is preferably performed thoroughly because the framework structure of the first precursor material (A1) for the ordered mesoporous material may collapse if the calcining treatment S1-3 described later is performed while a large amount of water derived from the first metal-containing solution or the washing liquid remains in the first precursor material (A1).

Step S1-3: Calcining Step

Next, the first precursor material (B1) is calcinated to form a first precursor material (C1). The precursor material (B1) is a product obtained through impregnating, with the first metal-containing solution, the first precursor material (A1) for forming the first support having a porous structure and including the zeolite-type compound.

The calcining is preferably carried out, for example, in the air under conditions at 350° C. or more and 850° C. or less for 2 hours or more and 30 hours or less. Such calcining treatment allows the growth of crystals of the metal component deposited by the impregnation in the pores for the ordered mesoporous material, so that the first metal fine particles are formed in the pores.

Step S1-4: Hydrothermal Treatment Step

Then, the first precursor material (C1), obtained through calcining the first precursor material (B1), and a first structure-directing agent are mixed to form a mixture solution, which is hydrothermally treated to form a first catalyst structure.

The first structure-directing agent is a template agent for directing the framework structure of the first support of the first catalyst structure. The first structure-directing agent may be, for example, a surfactant. The first structure-directing agent is preferably selected depending on the framework structure of the first support in the first catalyst structure, and preferred examples thereof include a surfactant such as tetramethylammonium bromide (TMABr), tetraethylammonium bromide (TEABr), tetrapropylammonium bromide (TPABr).

The first precursor material (C1) and the first structure-directing agent may be mixed during or before the hydrothermal treatment step. Any method may be used to prepare the mixture solution. The first precursor material (C1), the first structure-directing agent, and the solvent may be mixed at the same time, or the first precursor material (C1) and the first structure-directing agent may be separately dispersed into individual solvents, and then the resulting dispersion solutions may be mixed. The solvent may be, for example, water, an organic solvent such as an alcohol, or a mixed solvent thereof. Before the hydrothermal treatment, the mixture solution is preferably subjected to pH adjustment using an acid or a base.

The hydrothermal treatment may be carried out using a known method, for example, which is preferably performed in a closed vessel under conditions at 80° C. or more and 800° C. or less and 0 kPa or more and 2000 kPa or less for 5 hours or more and 240 hours or less. The hydrothermal treatment is also preferably performed in a basic atmosphere. Although the reaction mechanism is not necessarily clear, the hydrothermal treatment using the first precursor material (C1) as a starting material can gradually destroy the framework structure of the first precursor material (C1) for the ordered mesoporous material but can form a new framework structure (porous structure) for the first support of the first catalyst structure due to the action of the first structure-directing agent while the position of the first metal fine particles in the pores of the first precursor material (C1) substantially remains. The resulting first catalyst structure includes a first support of a porous structure and first metal fine particles in the first support, in which the first support has first channels connecting multiple first pores derived from the porous structure, and at least some of the first metal fine particles are located in first channels of the first support. In the embodiment, the hydrothermal treatment step includes preparing a solution of a mixture of the first precursor material (C1) and the first structure-directing agent and hydrothermally treating the first precursor material (C1) in the mixture solution. This step is non-limiting, and alternatively, the first precursor material (C1) may be hydrothermally treated without being mixed with the first structure-directing agent.

Preferably, the precipitate (first catalyst structure) resulting from the hydrothermal treatment is collected (e.g., filtered off) and then optionally washed, dried, and calcinated. The washing liquid may be water, an organic solvent such as an alcohol, or a mixed solution thereof. The drying may include natural drying overnight or so or drying at a high temperature of 150° C. or less. The drying is preferably performed thoroughly because the framework structure for the first support of the first catalyst structure may collapse if the calcining treatment is performed while a large amount of water remains in the precipitate. The calcining treatment may be performed, for example, in the air under conditions at 350° C. or more and 850° C. or less for 2 hours or more and 30 hours or less. During such calcining treatment, the first structure-directing agent is burned away from the first catalyst structure. Depending on the intended use, the first catalyst structure may be used as it is without undergoing the calcining treatment of the collected precipitate. For example, when the first catalyst structure is used in a high-temperature oxidative atmosphere environment, the structure-directing agent will be burned away by being exposed to the usage environment for a certain period of time. In such a case, the resulting first catalyst structure can be used without any modification since it is substantially the same as that obtained after the calcining treatment.

The method described above of producing the first catalyst structure is an exemplary method for the case where an oxidation-resistant metal species (e.g., noble metal) is used as the first metal element (M1) to form the metal-containing solution with which the first precursor material (A1) is to be impregnated.

An easily oxidizable metal species (e.g., Fe, Co, Ni) may also be used as the first metal element (M1) to form the metal-containing solution with which the first precursor material (A1) is to be impregnated. In such a case, after the hydrothermal treatment, the hydrothermally treated precursor material (C1) is preferably subjected to reduction treatment. When the metal-containing solution contains such an easily oxidizable metal species as the first metal element (M1), the metal component can be oxidized by heating in the steps (S1-3 and S1-4) after the impregnation step (S1-2). Accordingly, the support formed in the hydrothermal treatment step (S1-4) may contain metal oxide fine particles. In order to obtain a first catalyst structure including a first support containing first metal fine particles, therefore, the hydrothermal treatment is preferably followed by calcining treatment of the collected precipitate and then preferably followed by reduction treatment in a reducing gas atmosphere, such as hydrogen gas. The reduction treatment reduces fine particles of an oxide of the first metal element (M1) in the first support to form fine particles of the first metal element (M1) (first metal fine particles). As a result, a first catalyst structure is obtained including a first support containing first metal fine particles. It should be noted that such reduction treatment may be performed as needed. For example, if the first catalyst structure is used in a reducing atmosphere environment, the metal oxide fine particles can be reduced by being exposed to the usage environment for a certain period of time. In such a case, the resulting first catalyst structure can be used without any modification since it is substantially the same as that obtained after the reduction treatment.

Modifications of First Catalyst Structure 1

Figure 3:
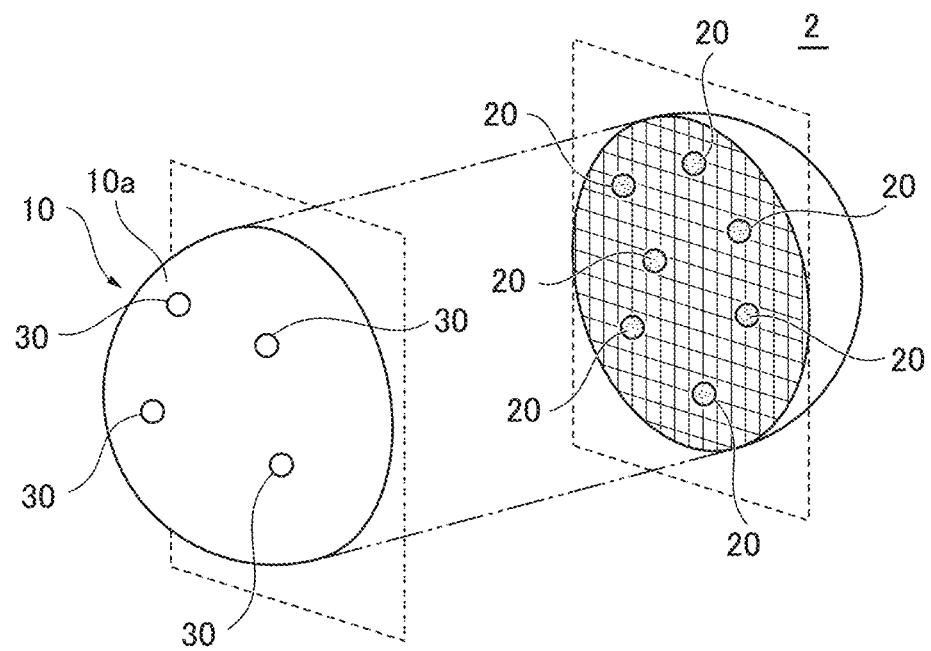
FIG. 3 is a schematic view showing a modification of the first catalyst structure of FIGS. 2(a) and 2(b).

FIG. 3 is a schematic view showing a modification of the first catalyst structure 1 of FIGS. 2(a) and 2(b), which will be referred to as a first catalyst structure 2. The catalyst structure 1 shown in FIGS. 2(a) and 2(b) includes the first support 10 and the first catalytic material 20 in the first support 10. Such a structure is non-limiting, and, as shown in FIG. 3, for example, a first catalyst structure 2 may be provided, which further includes an additional catalytic material 30 held on an outer surface 10a of the first support 10 in addition to the first catalytic material 20 in the first support 10.

The catalytic material 30 exerts one or more types of catalytic abilities. The catalytic ability of the additional catalytic material 30 may be the same as or different from that of the first catalytic material 20. The catalytic material 30 having the same catalytic ability as that of the first catalytic material 20 may be the same as or different from the first catalytic material 20. According to this configuration, the first catalyst structure 2 can have an increased catalytic material content, which further enhances the catalytic activity of the catalytic material.

In this case, the content of the first catalytic material 20 in the first support 10 is preferably higher than the content of the additional catalytic material 30 held on the outer surface 10a of the first support 10. In such a case, the catalytic ability of the first catalytic material 20 held inside the first support 10 can be dominant, and the first catalytic material can stably exhibit its catalytic ability.

Configuration of Second Catalyst Structure

The configuration of the second catalyst structure held in the second catalyst structure holder 108 of the hydrocarbon production apparatus 100 may be shown by substantially the same configuration as those for the first catalyst structure 1. For the sake of simplicity, therefore, the second catalyst structure will be described with reference to the schematic views of FIGS. 2(a) and 2(b) and FIG. 3, in which the term "first catalyst structure 1" will be replaced with "second catalyst structure", "first support 10" with "second support", "outer surface 10a of the first support" with "outer surface of the second support", "first channel 11" with "second channel", "first pore 11a" with "second pore", "first enlarged pore portion 12" with "second enlarged pore portion", "first small channel 13" with "second small channel", "first catalytic material 20" with "second metal fine particles", "the average particle size $D_{C1}$ of the first catalytic material 20" with "the average particle size $D_{C2}$ of the second metal fine particles", "the inner diameter $D_{E1}$ of the first enlarged pore portion 12" with "the inner diameter $D_{E2}$ of the second enlarged pore portion", and "the average inner diameter $D_{F1}$ of the first channels 11" with "the average inner diameter $D_{F2}$ of the second channels". The second catalyst structure is a catalyst suitable for use in FT synthesis reaction.

The second catalyst structure includes a second support having a porous structure and including a zeolite-type compound; and at least one second metal fine particles in the second support.

In the second catalyst structure, the second metal fine particles are included in the porous structure of the second support. The second metal fine particles are a catalytic material having a catalytic ability (catalytic activity). The second metal fine particles will be described in detail later. The metal fine particles 20 may be particles including a metal oxide, a metal alloy, or a composite of a metal oxide and a metal alloy.

As shown in FIG. 2 (b), the second support has a porous structure and has second channels communicating with outside the second support. The second support preferably has multiple second pores, which form the second channels. In the second support, some of the second channels have an average inner diameter of 0.95 nm or less, and the second metal fine particles are present in the second channels with an average inner diameter of 0.95 nm or less and preferably held in the second channels with an average inner diameter of 0.95 nm or less.

In particular, such a configuration increase the selectivity of the FT synthesis reaction for the hydrocarbons. Such a configuration also restrict the movement of the second metal fine particles in the second support and effectively prevents aggregation of the second metal fine particles. This results in effective prevention of a decrease in the effective surface area of the second metal fine particles and results in long-term retention of the catalytic activity of the second metal fine particles. In other words, the configuration of the second catalyst structure makes it possible to prevent a decrease in catalytic activity, which would otherwise be caused by aggregation of the second metal fine particles, and to prolong the life of the second catalyst structure. Moreover, thanks to the prolonged life of the second catalyst structure, the frequency of replacement of the second catalyst structure can be reduced, and the amount of discarding of the used second catalyst structure can be greatly reduced, which leads to resource saving.

In general, when used in a fluid (e.g., heavy oil, reforming gas such as $NO_x$), the second catalyst structure may receive an external force from the fluid. In the second catalyst structure, the pressure applied from the fluid onto the second metal fine particles held in the second channels becomes lower than that applied outside the second support as explained for the first catalyst structure 1. Therefore, the second metal fine particles are effectively prevented from separating from the second support, and the catalytic activity of the second metal fine particles can be stably maintained for a long period of time.

As in the first catalyst structure 1, the second channels 11 preferably have any one of a one-dimensional pore, a two-dimensional pore, and a three-dimensional pore, which are defined by the framework structure of the zeolite-type compound, and preferably have second enlarged pore portions different from the one-dimensional pore, the two-dimensional pore, and the three-dimensional pore. In this case, the second metal fine particles are preferably present at least in the second enlarged pore portions and more preferably included at least in the second enlarged pore portions. The second enlarged pore portion 12 also preferably connects multiple second pores to one another when the second pores form any of the one-dimensional pore, the two-dimensional pore, and the three-dimensional pore. According to this configuration, another channel different from the one-dimensional pore, the two-dimensional pore, or the three-dimensional pore is provided in the second support to exert the function of the second metal fine particles more effectively. Moreover, the movement of the second metal fine particles is further restricted in the second support, and the second metal fine particles are more effectively prevented from aggregating together or separating from the second support.

As a non-limiting configuration, a second metal fine particle 20 may be included in the enlarged pore portion 12. Alternatively, a second metal fine particle may be held in the second channel while partially protruding out of the second enlarged pore portion. Alternatively, a second metal fine particle may be partially embedded in a portion of the second channel other than the second enlarged pore portion (e.g., an inner wall portion of the second channel) or may be held by fixation or the like.

The second channel preferably has a three-dimensional structure including a branching or junction portion inside the second support, and the second enlarged pore portion is preferably provided at the branching or junction portion of the second channel.

The average inner diameter $D_{F2}$ of all second channels provided in the second support may be calculated from the average of the short and long diameters of the second pores, which form any of the one-dimensional pore, the two-dimensional pore, and the three-dimensional pore. The average inner diameter $D_{F2}$ of all second channels is typically 0.10 nm or more and 1.50 nm or less and preferably 0.49 nm or more and 0.95 nm or less. Carbon monoxide and hydrogen as raw materials for the FT synthesis reaction have molecular sizes of about 0.38 nm and about 0.29 nm, respectively. Therefore, the average inner diameter $D_{F2}$ of all second channels is preferably 0.40 nm or more and 1.50 nm or less, more preferably 0.49 nm or more and 0.95 nm or less, and even more preferably 0.49 nm or more and 0.70 nm or less. The inner diameter $D_{F2}$ of the second enlarged pore portion is typically 0.5 nm or more and 50 nm or less, preferably 1.1 nm or more and 40 nm or less, and more preferably 1.1 nm or more and 3.3 nm or less. The inner diameter $D_{F2}$ of the second enlarged pore portion depends, for example, on the pore size of the second precursor material (A2) described later and the average particle size $D_{C2}$ of the second metal fine particles to be included. The inner diameter $D_{E2}$ of the second enlarged pore portion is such that it is possible to include the second metal fine particle.

The second support includes a zeolite-type compound. Examples of the zeolite-type compound may be the same as those for the first catalyst structure 1. In particular, the zeolite-type compound is preferably a silicate compound.

The framework structure of the zeolite compound may be the same as that for the first catalyst structure 1 and is preferably MFI type, MOR type, or BEA type.

The zeolite-type compound has multiple pores with a diameter depending on its framework structure. For example, MFI type ([010] axis) has a short pore diameter of 0.53 nm (5.30 Å), a long pore diameter of 0.56 nm (5.50 Å), and an average pore diameter (average inner diameter) of about 0.55 nm (5.50 Å). If the reaction product has a size (typically a molecular size) smaller than the inner diameter of the second channels in the second support, which depends on the framework structure of the zeolite-type compound, the reaction product will be restricted from moving through the second channels. During the hydrocarbon synthesis, the carbon chain grows as the reactive material comes into contact with the second metal fine particles in the pores of the zeolite-type compound. In the second support including the zeolite-type compound, therefore, some of the second channels, specifically, second channels holding the second metal fine particles as a catalytic material have an average inner diameter $D_{T2}$ of 0.95 nm or less. This configuration can control the carbon chain growth based on the pore size of the zeolite-type compound and can suppress the production of heavy hydrocarbons with a relatively large molecular size. Thus, the second catalyst structure in which the average inner diameter $D_{T2}$ of some second channels holding the second metal fine particles is controlled to 0.95 nm or less as mentioned above can have high selectivity, for example, for production of the aromatic hydrocarbons and olefins having four or less carbon atoms in the Fischer-Tropsch synthesis reaction. Although depending on the framework structure of the zeolite-type compound, the average inner diameter $D_{T2}$ preferably has a lower limit of 0.39 nm or more for production of materials having three or more carbon atoms, which are useful as petrochemical raw materials. The pores in the zeolite-type compound are not always circular and may be polygonal in some cases. In such cases, the average inner diameter $D_{T2}$ may be calculated, for example, by evenly dividing the sum of the long pore diameters (long axes) and the short pore diameters (short axes) of the pores.

When the average inner diameter $D_{T2}$ of some second channels holding the second metal fine particles is more strictly controlled, the second catalyst structure can have higher selectivity for production of light hydrocarbons and in particular can have higher selectivity for production of light hydrocarbons having a molecular size substantially the same as the average inner diameter $D_{T2}$. For example, light hydrocarbons with three carbon atoms have a molecular size of 0.49 nm or more and less than 0.59 nm, light hydrocarbons with four carbon atoms have a molecular size of 0.59 nm or more and less than 0.70 nm, light hydrocarbons with five carbon atoms have a molecular size of 0.70 nm or more and less than 0.79 nm, and light hydrocarbons with six carbon atoms have a molecular size of 0.79 nm or more and less than 0.95 nm. N-Hexene with six carbon atoms has a molecular size of about 0.91 nm, n-pentene with five carbon atoms has a molecular size of about 0.78 nm, n-butene with four carbon atoms has a molecular size of about 0.65 nm, propylene with three carbon atoms has a molecular size of about 0.52 nm, and ethylene with two carbon atoms has a molecular size of about 0.39 nm. Therefore, some of the second channels preferably have an average inner diameter $D_{T2}$ of 0.75 nm or less in order to increase the selectivity for production of hydrocarbons with four or less carbon atoms, preferably have an average inner diameter $D_{T2}$ of less than 0.75 nm and more preferably 0.55 nm or more and less than 0.75 nm in order to increase the selectivity for production of hydrocarbons with four carbon atoms, such as n-butene, and more preferably have an average inner diameter $D_{T2}$ of 0.63 nm or more and less than 0.75 nm for higher selectivity for production of hydrocarbons with four carbon atoms than for production of hydrocarbons with three carbon atoms and for more selective collection of n-butene. In order to increase the selectivity for production of hydrocarbons with three carbon atoms, such as propylene, some of the second channels preferably have an average inner diameter $D_{T2}$ of less than 0.68 nm and more preferably more than 0.39 nm and less than 0.68 nm. The selectivity for production of light hydrocarbons is sometimes affected not only by the pore size of the zeolite-type compound but also by the framework structure of the zeolite-type compound, the motion of the produced light hydrocarbon molecules, and other factors. For example, when the framework structure of the zeolite-type compound is MFI type, the selectivity for production of such olefins as propylene and butene (n-butene and isobutene) tends to be high. Therefore, even for production of light hydrocarbons with a molecular size larger than the average inner diameter $D_{F2}$, the selectivity can be increased using the influence of these factors.

The second metal fine particles, which may be primary particles or secondary particles resulting from aggregation of primary particles, preferably have an average particle size $D_{C2}$ larger than the average inner diameter $D_{F2}$ of all second channels and equal to or smaller than the inner diameter $D_{E2}$ of the second enlarged pore portion ($D_{F2} < D_{C2} < D_{E2}$) The second metal fine particles with such a configuration are preferably provided in the second enlarged pore portions in the second channels, so that the movement of the second metal fine particles is restricted in the second support. Therefore, even when an external force is applied from a fluid to the second meal fine particles, the movement of the second metal fine particles is suppressed in the second support, so that the second metal fine particles dispersed in second channels of the second support and respectively provided in the second enlarged pore portions are effectively prevented from coming into contact with one another.

The second metal fine particles, which may be either of primary particles and secondary particles, preferably have an average particle size $D_{C2}$ of 0.08 nm or more. The ratio ($D_{C2}/D_{F2}$) of the average particle size $D_{C2}$ of the second metal fine particles to the average inner diameter $D_{F2}$ of all second channels is preferably 0.05 or more and 300 or less, more preferably 0.1 or more and 30 or less, even more preferably 1.1 or more and 30 or less, and furthermore preferably 1.4 or more and 3.6 or less. The content of the second metal element (M2) of the second metal fine particles is preferably 0.5 mass % or more and 7.6 mass % or less, more preferably 0.5 mass % or more and 6.9 mass % or less, even more preferably 0.5 mass % or more and 2.5 mass % or less, and most preferably 0.5 mass % or more and 1.5 mass % or less with respect to the mass of the second catalyst structure.

The second metal fine particles only have to include metal that is intact and not oxidized. For example, the second metal fine particles may include a single metal or a mixture of two or more metals. When used herein to indicate the component (material) of the second metal fine particles, the term "metal" is a generic term for a metallic material including one or more second metal elements, which is intended to include an elementary metal including a single second metal element (M2) and an alloy including two or more second metal elements (M2). In the environment where the catalyst structure is used, an oxide of the second metal element can be reduced to second metal fine particles. In such a case, the metal oxide may be deemed to be equivalent to second metal fine particles.

The second metal fine particles may include a first metal or first and second metals. The first metal may be at least one selected from the group consisting of ruthenium (Ru), nickel (Ni), iron (Fe), and cobalt (Co). The second metal may be at least one different from the first metal and selected from the group consisting of platinum (Pt), palladium (Pd), gold (Au), silver (Ag), copper (Cu), ruthenium (Ru), iridium (Ir), rhodium (Rh), osmium (Os), zirconium (Zr), and manganese (Mn). When the second metal is Ru, the first metal may be at least one selected from the group consisting of Ni, Fe, and Co. In particular, to be useful for the FT synthesis reaction, the second metal fine particles preferably include at least one of Co, Fe, Ni, and Ru. For higher catalytic activity for the FT synthesis reaction, the second metal fine particles preferably include the second metal in addition to the first metal selected from Co, Fe, Ni, and Ru.

The ratio (Si/M atomic ratio) of the number of silicon (Si) atoms in the second support to the number of the second metal element (M2) in the second metal fine particles is preferably 10 or more and 1000 or less, more preferably 50 or more and 200 or less, and even more preferably 100 or more and 200 or less. If the ratio is higher than 1000, the second metal fine particles may have low catalytic activity or fail to act sufficiently as a catalytic material. If the ratio is lower than 10, the content of the second metal fine particles 20 may be so high as to tend to reduce the strength of the second support. It should be noted that, in this context, the term "second metal fine particles" refers to fine particles held or supported inside the second support and is not intended to include metal fine particles deposited on the outer surface of the second support.

Function of Second Catalyst Structure

As mentioned above, the second catalyst structure includes a second support of a porous structure and at least one second metal fine particles in the second support. When brought into contact with a fluid, the second catalyst structure exerts the catalytic ability of the second metal fine particles in the second support. Specifically, when coming into contact with the outer surface of the second catalyst structure, the fluid is allowed to flow into the interior of the second support through a second pore at the outer surface, guided into the second channels, and allowed to pass through the second channels and to flow out of the second catalyst structure through another second pore. The second metal fine particles in some channels with an average inner diameter of 0.95 nm or less among the second channels cause a catalytic reaction when coming into contact with the fluid passing through the second channels. The second catalyst structure also has a molecular sieving ability since the second support has a porous structure.

First, the molecular sieving ability of the second catalyst structure will be described with reference to an example in which the fluid includes carbon monoxide and hydrogen. The second catalyst structure may be brought into contact with carbon monoxide and hydrogen sequentially or simultaneously.

Compound molecules (e.g., carbon monoxide and hydrogen) having a size equal to or smaller than the diameter of the second pore, in other words, equal to or smaller than the inner diameter of the second channel, can enter the second support. On the other hand, gas component molecules having a size exceeding the diameter of the second pore cannot enter the second support. Accordingly, among multiple compounds in the fluid, some compounds not capable of entering the second support are restricted from reacting, and some other compounds capable of entering the second support are allowed to react.

Among compounds produced by reactions in the second support, only compounds having a molecular size not exceeding the diameter of the second pore can pass through the second pore to outside the second support to obtain a reaction product. On the other hand, some compounds are not capable of passing through the second pore to outside the second support. If such compounds are converted into compounds having a molecular size that allows exit from the second support, the compounds can go outside the second support. Even with a size larger than the second pore diameter, some produced compound molecules in motion can go outside the second support while expanding and contracting. Therefore, a specific reaction product can be selectively obtained using the second catalyst structure in which the diameter of second pores is controlled, specifically, the diameter of second pores holding the second metal fine particles is controlled. In this embodiment, specifically, carbon monoxide and hydrogen react to yield hydrocarbons as reaction products, which includes lower olefins including propylene and aromatic hydrocarbons having six or more and ten or less carbon atoms.

In the second catalyst structure, the second metal fine particles may be included in the second enlarged pore portions of the second channels. When the average particle size $D_{C2}$ of the second metal fine particles is larger than the average inner diameter $D_{T2}$ of some of the second channels and smaller than the inner diameter $D_{E2}$ of the second enlarged pore portion ($D_{T2} < D_{C2} < D_{E2}$), a small second channel is provided between the second metal fine particle and the second enlarged pore portion. In this case, the fluid entering the second small channel comes into contact with the second metal fine particle. Each second metal fine particle included in the second enlarged pore portion is restricted from moving in the second support. Thus, the second metal fine particles are prevented from aggregating in the second support 10. As a result, a large contact area can be stably maintained between the second metal fine particles and the fluid.

Specifically, when a molecule (a material to be reformed) entering the second channel comes into contact with the second metal fine particles, a catalytic reaction occurs to reform the molecule. For example, lower olefins and the aromatic hydrocarbons can be selectively produced from a mixed gas composed mainly of hydrogen and carbon monoxide as raw materials by using the second catalyst structure with controlled average inner diameter $D_{T2}$ of some of the second channels. The FT synthesis reaction of hydrogen and carbon monoxide as main components, although carried out, for example, at a high temperature of 350° C. or more and 550° C. or less, is less affected by the heating, since the second metal fine particles are incorporated in the second support. In particular, the second metal fine particles inside the second enlarged pore portions are more restricted from moving in the second support, so that the second metal fine particles are more effectively prevented from aggregating (sintering). As a result, a decrease in catalytic activity is more effectively prevented, which allows the second catalyst structure to have a longer life. Even if the second catalyst structure has reduced catalytic activity after long-term use, the second metal fine particles, which are not bonded to the second support, can be easily activated (reduced).

Method of Producing Second Catalyst Structure

The second catalyst structure may be produced using a method basically similar to that for the first catalyst structure 1. Therefore, among the configuration of the method of producing the second catalyst structure, a configuration different from those of the method of producing the first catalyst structure 1 will be described while the same configuration is omitted.

Step S2-1: Preparation Step

First, a second precursor material (A2) is prepared, which is for forming a second support having a porous structure and including a zeolite-type compound.

When a silicate compound is used as the zeolite-type compound for forming the support of the second catalyst structure, an ordered mesoporous material may be formed in the same manner as for the first catalyst structure 1.

The second precursor material (A2) may be prepared in the same manner as for the first catalyst structure 1.

Step S2-2: Impregnation Step

Next, the prepared second precursor material (A2) is impregnated with a second metal-containing solution to form a second precursor material (B2).

The second metal-containing solution may be any solution containing a metal component (e.g., metal ions) corresponding to the second metal element (M2) for forming the second metal fine particles. For example, the second metal-containing solution may be prepared by dissolving, in a solvent, a metal salt containing the second metal element (M2). Examples of such a metal salt include chlorides, hydroxides, oxides, sulfates, and nitrates, among which nitrates are preferred. The solvent may be, for example, water, an organic solvent such as an alcohol, or a mixture solvent thereof.

The same method as for the first catalyst structure 1 may be used to impregnate the second precursor material (A2) with the second metal-containing solution.

The amount of the second metal element (M2) in the second metal-containing solution, with which the second precursor material (A2) is to be impregnated (in other words, the amount of the second metal element (M2) to be incorporated into the second precursor material (B2)) is preferably taken into account when the amount of the second metal-containing solution added to the second precursor material (A2) is appropriately adjusted. For example, prior to the calcining step S2-3 described later, the amount of addition of the second metal-containing solution to the second precursor material (A2) is preferably adjusted such that the ratio (Si/M atomic ratio) of the number of silicon (Si) atoms in the second precursor material (A2) to the number of the second metal element (M2) in the second metal-containing solution is set to 10 or more and 1000 or less, more preferably 50 or more and 200 or less, and even more preferably 100 or more and 200 or less.

The impregnation of the second precursor material (A2) with the second metal-containing solution may be followed by the same treatment as for the first catalyst structure 1.

Step S2-3: Calcining Step

Next, the second precursor material (B2) is calcinated to form a second precursor material (C2). The second precursor material (B2) is a product obtained through impregnating, with the second metal-containing solution, the second precursor material (A2) for forming the second support having a porous structure and including the zeolite-type compound. The calcining treatment may be the same as for the first catalyst structure 1.

Step S2-4: Hydrothermal Treatment Step

Then, the second precursor material (C2), obtained through calcining the second precursor material (B2), and a second structure-directing agent are mixed to form a mixture solution, which is hydrothermally treated to form a second catalyst structure.

The second structure-directing agent is a template agent for directing the framework structure of the second support of the second catalyst structure, which may be, for example, a surfactant. The second structure-directing agent is preferably selected depending on the framework structure of the second support in the second catalyst structure, and preferred examples thereof include a surfactant such as tetramethylammonium bromide (TMABr), tetraethylammonium bromide (TEABr), tetrapropylammonium bromide (TPABr), tetraethylammonium hydroxide (TEAOH).

The same method as for the first catalyst structure 1 may be used for mixing the second precursor material (C2) and the second structure-directing agent to form a mixture solution.

A known method may be used to carry out the hydrothermal treatment. For example, the same method as for the first catalyst structure 1 may be used for the hydrothermal treatment. Although the reaction mechanism is not necessarily clear, the hydrothermal treatment using the second precursor material (C2) as a starting material can gradually destroy the framework structure of the second precursor material (C2) for the ordered mesoporous material but can form a new framework structure (porous structure) for the second support of the second catalyst structure due to the action of the second structure-directing agent while the position of the second metal fine particles in the pores of the second precursor material (C2) substantially remains. The resulting second catalyst structure includes a second support of a porous structure and second metal fine particles present in the second support, in which the second support has second channels connecting multiple second pores derived from the porous structure, and at least some of the second metal fine particles are located in second channels of the second support. In the embodiment, the hydrothermal treatment step includes preparing a solution of a mixture of the second precursor material (C2) and the second structure-directing agent and hydrothermally treating the second precursor material (C2) in the mixture solution. This step is non-limiting, and alternatively, the second precursor material (C2) may be hydrothermally treated without being mixed with the second structure-directing agent.

Preferably, the precipitate (second catalyst structure) resulting from the hydrothermal treatment is collected (e.g., filtered off) and then, for example, optionally washed, dried, and calcinated in the same manner as for the first catalyst structure 1.

The method described above of producing the second catalyst structure is an exemplary method for the case where an oxidation-resistant metal species (e.g., noble metal) is used as the second metal element (M2) to form the second metal-containing solution with which the second precursor material (A2) is to be impregnated.

An easily oxidizable metal species (e.g., Fe, Co, Ni) may also be used as the second metal element (M2) to form the metal-containing solution with which the second precursor material (A2) is to be impregnated. In such a case, after the hydrothermal treatment, the hydrothermally treated second precursor material (C2) is preferably subjected to reduction treatment. When the metal-containing solution contains such an easily oxidizable metal species as the second metal element (M2), the metal component can be oxidized by heating in the steps (S2-3 and S2-4) after the impregnation step (S2-2). Accordingly, the support formed in the hydrothermal treatment step (S2-4) may contain metal oxide fine particles. In order to obtain a second catalyst structure including a second support containing second metal fine particles, the hydrothermal treatment is preferably followed by calcining treatment of the collected precipitate and then preferably followed by reduction treatment in a reducing gas atmosphere, such as hydrogen gas. The reduction treatment reduces the metal oxide fine particles in the second support to form fine particles of the second metal element (M2) (second metal fine particles). As a result, a second catalyst structure is obtained including a second support containing second metal fine particles. It should be noted that such reduction treatment may be performed as needed. For example, if the second catalyst structure is used in a reducing atmosphere environment, the metal oxide fine particles can be reduced by being exposed to the usage environment for a certain period of time. In such a case, the second catalyst structure containing oxide fine particles in the second support may be used as it is since it can be reduced in the usage environment as in the reduction treatment.

Modifications of Second Catalyst Structure

Modifications of the second catalyst structure may be basically the same as those of the first catalyst structure. For the sake of simplicity, therefore, modifications of the second catalyst structure are described herein with the term "first catalyst structure 2" (modified example) replaced with "second catalyst structure".

As a non-limiting example, the second catalyst structure includes the second support and the second metal fine particles in the second support. Alternatively, the second catalyst structure may further include at least one additional catalytic material 30 held on an outer surface of the second support in addition to the second metal fine particles in the second support.

The catalytic material 30 exerts one or more types of catalytic abilities. The catalytic ability of the additional catalytic material 30 may be the same as or different from that of the second metal fine particles. The catalytic material 30 having the same catalytic ability as that of the second metal fine particles may be the same as or different from the material of the second metal fine particles. According to this configuration, the second catalyst structure can have an increased catalytic material content, which further enhances the catalytic activity of the catalytic material.

In this case, the content of the second metal fine particles in the second support is preferably higher than the content of the additional catalytic material 30 held on the outer surface of the second support. In such a case, the catalytic ability of the second metal fine particles held inside the second support can be dominant, and the second catalytic material can stably exhibit its catalytic ability.

While a hydrocarbon production apparatus and a hydrocarbon production method according to embodiments of the present invention have been described, it will be understood that the embodiments are not intended to limit the present invention and may be altered or modified in various ways based on the technical idea of the present invention.

EXAMPLES

Example 1-1

First, first catalyst structure E1-1 shown in Table 1 was used. First catalyst structure E1-1 included a support and Ni as a first catalytic material (in the form of first metal fine particles), which was provided in the support and held on the outer surface of the support. First catalyst structure E1-1 was placed in the interior of a synthesis gas production unit. Subsequently, while first catalyst structure E1-1 was heated at 700° C., methane and carbon dioxide in a volume ratio of 1:1 were supplied (GHSV=5,600 $h^{-1}$) to the synthesis gas production unit over five hours, and the presence or absence of carbon monoxide and hydrogen in the gas discharged from the synthesis gas production unit was determined using a detector. As a result, the detector detected carbon monoxide and hydrogen, which indicated that the synthesis gas production unit successfully produced a synthesis gas.

Evaluation 1

Next, an evaluation was made on the methane conversion rate and on the presence or absence of deposition of carbon.

(1-1) Methane Conversion Rate

The amount (M1) of methane supplied to the synthesis gas production unit and the amount (M2) of methane discharged from the synthesis gas production unit were measured and then used to calculate the methane conversion rate using the formula (M1−M2)×100/M1. The higher the methane conversion rate, the larger the amount of produced carbon monoxide and hydrogen. A methane conversion rate of 40% or more was evaluated to indicate good catalytic activity (o), and a methane conversion rate of less than 40% was evaluated to indicate poor catalytic activity (x).

(1-2) Presence or Absence of Deposition of Carbon

The presence or absence of deposition of carbon (coking) on first catalyst structure E1-1 was determined using a CHN elemental analysis system (CE-440 (trade name) manufactured by Exeter Analytical, Inc.).

Comparative Examples 1-1 and 1-2

Comparative Examples 1-1 and 1-2 were carried out in the same manner as Example 1-1 except that catalyst structure C1-1 or catalyst structure C1-2 shown in Table 1 was used instead of first catalyst structure E1-1. Evaluations were then made in the same manner as for Example 1-1. Catalyst structures C1-2 and C1-2 each included a solid alumina support with no zeolite structure; and Ni provided by impregnation method and supported on the alumina support, in which Ni was held only on the outer surface of the support and not located inside the support.

Table 1 shows the conditions for the pretreatment of the catalyst structures, the conditions for the reaction in the synthesis gas production unit, and the evaluation results.

aromatic hydrocarbons in the gas discharged from the hydrocarbon production unit was determined using a detector. As a result, the detector detected olefins with four or less carbon atoms, including propylene, and the aromatic hydrocarbons having six or more and ten or less carbon atoms mentioned above, which indicated that the hydrocarbon production unit successfully produced desired hydrocarbons. The synthesis gas supplied to the hydrocarbon production unit was the synthesis gas obtained in the synthesis gas production unit in Example 1-1, in which the methane conversion rate was good and carbon deposition was not observed.

Evaluation 2

Next, an evaluation was made on each of the degree of selectivity for production of lower olefins and that for production of aromatic hydrocarbons.

(2-1) Degree of Selectivity for Production of Lower Olefins

The degree of selectivity for production of lower olefins (olefins having four or less carbon atoms) was defined as the content of the lower olefins in the hydrocarbons in the reaction product. A degree of selectivity of 10% or more was evaluated as good (o), and a degree of selectivity of less than 10% was evaluated as poor (x).

(2-2) Degree of Selectivity for Production of Aromatic Hydrocarbons

The degree of selectivity for production of the aromatic hydrocarbons (having six or more and ten or less carbon atoms) was defined as the content of the aromatic hydrocarbons in the hydrocarbons in the reaction product. A degree of selectivity of 5% or more was evaluated as good (o), a degree of selectivity of 1% or more and less than 5% as fair (A), and a degree of selectivity of less than 1% as poor (x).

TABLE 1

|  |  | Example | Comparative Example | |
|---|---|---|---|---|
|  |  | 1-1<br>First catalyst structure E1-1 | 1-1<br>Catalyst structure C1-1 | 1-2<br>Catalyst structure C1-2 |
| Catalyst structure | Support | Zeolite-type compound | $Al_2O_3$ | $Al_2O_3$ |
|  | First catalytic material | Ni (first metal fine particles) | Ni (first metal fine particles) | Ni (first metal fine particles) |
|  | First catalytic material content (mass %) | 1% | 66% | 1% |
|  | Location of first catalytic material | Inside and outer surface of support | Outer surface of support | Outer surface of support |
|  | Pretreatment conditions (reduction conditions) | | 700° C./1.5 h/$H_2$ | |
| Reaction conditions | Raw material gas (volume ratio) | | $CH_4$:$CO_2$ = 1:1 | |
|  | Reaction temperature (° C.) | | 700° C. | |
| Evaluation | Methane conversion rate | ○ | ○ | x |
|  | Carbon deposition | Absent | Present | Present |

Example 2-1

First, second catalyst structure E2-1 shown in Table 2 was used. Second catalyst structure E2-1 included a support and Co as a second catalytic material (in the form of second metal fine particles), which was present in the support and held on the outer surface of the support. Second catalyst structure E2-1 was placed in the interior of a hydrocarbon production unit. Subsequently, while second catalyst structure E2-1 was heated at 400° C. and 500° C., a synthesis gas was supplied (GHSV=3000 h$^{-1}$) to the hydrocarbon production unit, and the presence or absence of lower olefins and Comparative Example 2-1

Comparative Example 2-1 was carried out in the same manner as Example 2-1 except that catalyst structure C2-1 shown in Table 2 was used instead of second catalyst structure E2-1. Evaluations were made in the same manner as for Example 2-1. Catalyst structure C2-1 included a support having a porous structure and including a zeolite-type compound; and Co held on the outer surface of the support, in which Co was held only on the outer surface of the support and not located inside the support.

Table 2 shows the conditions for the pretreatment of the catalyst structures, the conditions for the reaction in the hydrocarbon production unit, and the evaluation results.

TABLE 2

|  |  | Example 2-1<br>Second catalyst structure E2-1 | Comparative Example 2-1<br>Catalyst structure C2-1 |
|---|---|---|---|
| Catalyst structure | Support | Zeolite-type compound | Zeolite-type compound |
|  | Second catalytic material | Co (second metal fine particles) | Co (second metal fine particles) |
|  | Second catalytic material content (mass %) | 1% | 1% |
|  | Location of second catalytic material | Inside and outer surface of support | Outer surface of support |
|  | Pretreatment conditions (reduction conditions) | 500° C./1 h/$H_2$ | |
| Reaction conditions | synthesis gas | Synthesis gas produced in Example 1-1 | |
|  | Reaction temperature (° C.) | 400° C. and 500° C. | |
| Evaluation | Lower olefin selectivity (400° C.) | ◯ | x |
|  | Lower olefin selectivity (500° C.) | ◯ | x |
|  | Aromatic hydrocarbon selectivity (400° C.) | Δ | x |
|  | Aromatic hydrocarbon selectivity (500° C.) | ◯ | x |

The results in Tables 1 and 2 show that the production apparatus according to Examples 1-1 and 2-1 successfully operated continuously for a long period of time with no deposition of carbon observed on the first catalyst structure. The results also show that the degree of selectivity was high for production of the desired hydrocarbons. The results demonstrate that the desired hydrocarbons were produced with improved selectivity and with less decrease in catalytic activity by a process including: producing a synthesis gas including carbon monoxide and hydrogen from methane and carbon dioxide in the raw material gas using the first catalyst structure being heated in the synthesis gas production unit; and producing, from carbon monoxide and hydrogen in the synthesis gas, lower olefins including propylene and aromatic hydrocarbons with six or more and ten or less carbon atoms using the second catalyst structure being heated in the hydrocarbon production unit.

EXPLANATION OF REFERENCE NUMERALS

100: Hydrocarbon production apparatus
101: First supply unit
102a: Methane supply unit
102b: Carbon dioxide supply unit
103: Synthesis gas production unit
104: First catalyst structure holder
105: First separation unit
106: Second supply unit
107: Hydrocarbon production unit
108: Second catalyst structure holder
109: First detection unit
110: Fourth separation unit
111: Second separation unit
112: Fifth separation unit
113: Third separation unit
114: Oxygen supply unit
115: Second detection unit
116: Third supply unit
117: Fourth supply unit
118: Fifth supply unit
1, 2: First catalyst structure
10: First support
10a: Outer surface of the first support
11: First channel
11a: First pore
12: First enlarged pore portion
13: First small channel
20: First catalytic material
30: Catalytic material

The invention claimed is:

1. An apparatus for producing hydrocarbons including lower olefins including propylene and aromatic hydrocarbons having six or more and ten or less carbon atoms, the apparatus comprising:
   a first supply unit that supplies a raw material gas comprising methane and carbon dioxide;
   a synthesis gas production unit that comprises a first catalyst structure, receives supply of the raw material gas from the first supply unit, and produces a synthesis gas comprising carbon monoxide and hydrogen from methane and carbon dioxide in the raw material gas while heating the first catalyst structure;
   a second supply unit that supplies the synthesis gas discharged from the synthesis gas production unit;
   a hydrocarbon production unit that comprises a second catalyst structure, receives supply of the synthesis gas from the second supply unit, and produces, from carbon monoxide and hydrogen in the synthesis gas, hydrocarbons including lower olefins including propylene and aromatic hydrocarbons having six or more and ten or less carbon atoms while heating the second catalyst structure; and
   a first detection unit that detects propylene and the aromatic hydrocarbons in the hydrocarbons discharged from the hydrocarbon production unit, wherein
   the first catalyst structure includes first supports each having a porous structure and including a zeolite-type compound, and at least one first catalytic material present in the first supports,
   the first supports have first channels communicating with outside the first supports,
   the first catalytic material is in the form of first metal fine particle and is present at least in the first channels of the first supports, the second catalyst structure includes second supports each having a porous structure and including a zeolite-type compound, and at least one second metal fine particle present in the second supports, the second supports have second channels communicating with outside the second supports, and some of the second channels have an average inner diameter of 0.95 nm or less.

2. The apparatus for producing hydrocarbons according to claim 1, wherein the aromatic hydrocarbons include at least one of a polycyclic aromatic hydrocarbon and a compound represented by formula (1):

[Chem. 1]

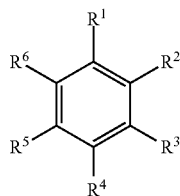

formula (1)

wherein $R^1$, $R^2$, $R^3$, $R^4$, $R^5$, and $R^6$ are each independently a hydrogen atom or an alkyl group having one or more and four or less carbon atoms.

3. The apparatus for producing hydrocarbons according to claim 2, wherein the compound represented by formula (1) includes one or more compounds selected from the group consisting of benzene, toluene, and butylbenzene.

4. The apparatus for producing hydrocarbons according to claim 2, wherein the polycyclic aromatic hydrocarbon includes at least one of azulene and naphthalene.

5. The apparatus for producing hydrocarbons according to claim 1, further comprising an oxygen supply unit that supplies oxygen to the synthesis gas production unit.

6. The apparatus for producing hydrocarbons according to claim 1, wherein the synthesis gas production unit heats the first catalyst structure at 600° C. or more and 1000° ° C. or less.

7. The apparatus for producing hydrocarbons according to claim 1, wherein the first metal fine particle is a fine particle comprising at least one metal selected from the group consisting of rhodium (Rh), ruthenium (Ru), iridium (Ir), palladium (Pd), platinum (Pt), iron (Fe), cobalt (Co), and nickel (Ni).

8. The apparatus for producing hydrocarbons according to claim 1, wherein the first channels have any one of a one-dimensional pore, a two-dimensional pore, and a three-dimensional pore of a framework structure of the zeolite-type compound, and have a first enlarged pore portion different from the one-dimensional pore, the two-dimensional pore, and the three-dimensional pore, and the first catalytic material is present at least in the first enlarged pore portion.

9. The apparatus for producing hydrocarbons according to claim 1, further comprising a first separation unit that separates methane and carbon dioxide in the synthesis gas discharged from the synthesis gas production unit.

10. The apparatus for producing hydrocarbons according to claim 9, further comprising a third supply unit that supplies, to the synthesis gas production unit, methane and carbon dioxide separated by the first separation unit.

11. The apparatus for producing hydrocarbons according to claim 1, further comprising a second detection unit that detects carbon monoxide and hydrogen in the synthesis gas discharged from the synthesis gas production unit.

12. The apparatus for producing hydrocarbons according to claim 1, wherein the hydrocarbon production unit heats the second catalyst structure at 350° C. or more and 550° C. or less.

13. The apparatus for producing hydrocarbons according to claim 1, wherein the second metal fine particle comprises at least one first metal selected from the group consisting of ruthenium (Ru), nickel (Ni), iron (Fe), and cobalt (Co) or comprises at least one first metal selected from the group consisting of ruthenium (Ru), nickel (Ni), iron (Fe), and cobalt (Co) and at least one second metal being different from the first metal and selected from the group consisting of platinum (Pt), palladium (Pd), gold (Au), silver (Ag), copper (Cu), ruthenium (Ru), iridium (Ir), rhodium (Rh), osmium (Os), zirconium (Zr), and manganese (Mn).

14. The apparatus for producing hydrocarbons according to claim 1, wherein some of the second channels have an average inner diameter of 0.39 nm or more and 0.75 nm or less.

15. The apparatus for producing hydrocarbons according to claim 1, wherein the second channels have any one of a one-dimensional pore, a two-dimensional pore, and a three-dimensional pore of a framework structure of the zeolite-type compound, and have a second enlarged pore portion different from the one-dimensional pore, the two-dimensional pore, and the three-dimensional pore, and the second metal fine particle is present at least in the second enlarged pore portion.

16. The apparatus for producing hydrocarbons according to claim 1, further comprising a second separation unit that separates hydrogen, carbon monoxide, and the hydrocarbons discharged from the hydrocarbon production unit.

17. The apparatus for producing hydrocarbons according to claim 16, further comprising a fourth supply unit that supplies, to the hydrocarbon production unit, carbon monoxide and hydrogen separated by the second separation unit.

18. The apparatus for producing hydrocarbons according to claim 1, further comprising a third separation unit that separates carbon dioxide, methane, and the hydrocarbons discharged from the hydrocarbon production unit.

19. The apparatus for producing hydrocarbons according to claim 18, further comprising a fifth supply unit that supplies, to the synthesis gas production unit, methane and carbon dioxide separated by the third separation unit.

20. The apparatus for producing hydrocarbons according to claim 1, further comprising a fourth separation unit that cools the hydrocarbons discharged from the hydrocarbon production unit and separates the lower olefins and the aromatic hydrocarbons.

* * * * *